(12) United States Patent
Yellin et al.

(10) Patent No.: US 11,103,349 B2
(45) Date of Patent: Aug. 31, 2021

(54) DEVICES AND METHODS FOR THE TREATMENT OF HEART VALVE INSUFFICIENCIES

(71) Applicant: VALCARE, INC., Newport Beach, CA (US)

(72) Inventors: Nadav Yellin, Ramat Gan (IL); Samuel M. Shaolian, Newport Beach, CA (US); Matan Gedulter, Givat Ella (IL); Boaz Schwarz, Tel Aviv (IL); Daniel Rapoport, Kfar Menahem (IL); Avraham Eftel, Tel Aviv (IL)

(73) Assignee: VALCARE, INC., Newport Beach, CA (US)

( * ) Notice: Subject to any disclaimer, the term of this patent is extended or adjusted under 35 U.S.C. 154(b) by 9 days.

(21) Appl. No.: 15/677,408

(22) Filed: Aug. 15, 2017

(65) Prior Publication Data

US 2018/0042723 A1 Feb. 15, 2018

Related U.S. Application Data

(60) Provisional application No. 62/375,079, filed on Aug. 15, 2016.

(51) Int. Cl.
*A61F 2/24* (2006.01)
*A61F 2/00* (2006.01)

(52) U.S. Cl.
CPC .......... *A61F 2/2448* (2013.01); *A61F 2/0077* (2013.01); *A61F 2/2466* (2013.01); *A61F 2002/0081* (2013.01); *A61F 2210/0014* (2013.01); *A61F 2220/0016* (2013.01); *A61F 2220/0033* (2013.01); *A61F 2250/001* (2013.01)

(58) Field of Classification Search
CPC .................. A61F 2/2445; A61F 2/2448; A61F 2220/0016; A61F 2/2427; A61F 2/243; A61F 2/2436; A61F 2/2439; A61F 2/2466
See application file for complete search history.

(56) References Cited

U.S. PATENT DOCUMENTS

| 4,602,911 A | 7/1986 | Ahmadi et al. |
| 5,236,440 A | 8/1993 | Hlavacek |

(Continued)

FOREIGN PATENT DOCUMENTS

| DE | 102014102653 A1 | 9/2015 |
| EP | 2600799 A | 6/2013 |

(Continued)

OTHER PUBLICATIONS

International Search Report and Written Opinion for PCT/US2018/022910 dated May 23, 2018.

(Continued)

*Primary Examiner* — Majid Jamialahmadi
(74) *Attorney, Agent, or Firm* — Stoel Rives LLP

(57) ABSTRACT

Disclosed herein are various embodiments directed to a device for minimally invasive medical treatment. The device being a hollow tube with a first end, a second end, and one or more anchors configured to extend outward from the exterior of the hollow tube. The hollow tube having a plurality of cutouts on the exterior, wherein the cutouts allow the hollow tube to be flexible. Additionally, the hollow tube may have at least one snap mechanism configured to connect the first end and the second end together.

10 Claims, 56 Drawing Sheets

(56) References Cited

U.S. PATENT DOCUMENTS

| | | |
|---|---|---|
| 5,306,296 A | 4/1994 | Wright et al. |
| 5,695,518 A | 12/1997 | Laerum |
| 5,716,370 A | 2/1998 | Williamson, IV et al. |
| 5,855,614 A | 1/1999 | Stevens et al. |
| 6,113,611 A | 9/2000 | Allen et al. |
| 6,231,602 B1 | 5/2001 | Carpentier et al. |
| 6,619,291 B2 | 9/2003 | Hlavka et al. |
| 6,629,534 B1 | 10/2003 | St. Goar et al. |
| 6,669,687 B1 | 12/2003 | Saadat |
| 6,689,048 B2 | 2/2004 | Vanden Hoek et al. |
| 6,726,704 B1 | 4/2004 | Loshakove et al. |
| 6,776,784 B2 | 8/2004 | Ginn |
| 6,790,229 B1 | 9/2004 | Berreklouw |
| 6,797,002 B2 | 9/2004 | Spence et al. |
| 6,805,711 B2 | 10/2004 | Dugan et al. |
| 6,893,459 B1 | 5/2005 | Macoviak |
| 7,101,395 B2 | 9/2006 | Tremulis et al. |
| 7,114,953 B1 | 10/2006 | Wagner |
| 7,175,660 B2 | 2/2007 | Cartledge et al. |
| 7,238,191 B2 | 7/2007 | Bachmann |
| 7,285,087 B2 | 10/2007 | Moaddeb et al. |
| 7,297,150 B2 | 11/2007 | Cartledge et al. |
| 7,569,072 B2 | 8/2009 | Berg et al. |
| 7,594,887 B2 | 9/2009 | Moaddeb et al. |
| 7,635,329 B2 | 12/2009 | Goldfarb et al. |
| 7,655,040 B2 | 2/2010 | Douk et al. |
| 7,717,954 B2 | 5/2010 | Solem et al. |
| 7,722,668 B2 | 5/2010 | Moaddeb et al. |
| 7,758,637 B2 | 7/2010 | Starksen et al. |
| 7,837,729 B2 | 11/2010 | Gordon et al. |
| 7,988,725 B2 | 8/2011 | Gross et al. |
| 8,163,014 B2 | 4/2012 | Lane et al. |
| 8,182,529 B2 | 5/2012 | Gordon et al. |
| 8,236,049 B2 | 8/2012 | Rowe et al. |
| 8,287,591 B2 | 10/2012 | Keidar et al. |
| 8,518,107 B2 | 8/2013 | Tsukashima et al. |
| 8,579,968 B1 | 11/2013 | Shannon et al. |
| 9,180,008 B2 | 11/2015 | Yellin et al. |
| 9,402,721 B2 | 8/2016 | Buchbinder et al. |
| 9,433,503 B2 | 9/2016 | Tsukashima et al. |
| 2002/0151961 A1 | 10/2002 | Lashinski et al. |
| 2002/0151970 A1 | 10/2002 | Garrison et al. |
| 2002/0188170 A1 | 12/2002 | Santamore et al. |
| 2003/0050693 A1 | 3/2003 | Quijano et al. |
| 2003/0078465 A1 | 4/2003 | Pai et al. |
| 2003/0078671 A1 | 4/2003 | Lesniak et al. |
| 2003/0191528 A1 | 10/2003 | Quijano et al. |
| 2003/0198605 A1 | 10/2003 | Montgomery |
| 2003/0199974 A1 | 10/2003 | Lee et al. |
| 2004/0044364 A1 | 3/2004 | DeVries et al. |
| 2004/0068276 A1 | 4/2004 | Golden et al. |
| 2004/0122514 A1 | 6/2004 | Fogarty et al. |
| 2004/0138744 A1 | 7/2004 | Lashinski et al. |
| 2004/0148021 A1 | 7/2004 | Cartledge et al. |
| 2004/0193191 A1 | 9/2004 | Starksen et al. |
| 2004/0243230 A1 | 12/2004 | Navia et al. |
| 2004/0249391 A1 | 12/2004 | Cummins |
| 2004/0260393 A1 | 12/2004 | Randert et al. |
| 2004/0260394 A1 | 12/2004 | Douk et al. |
| 2005/0020696 A1 | 1/2005 | Montgomery et al. |
| 2005/0033325 A1 | 2/2005 | May et al. |
| 2005/0065550 A1 | 3/2005 | Starksen et al. |
| 2005/0090846 A1 | 4/2005 | Pedersen et al. |
| 2005/0096740 A1 | 5/2005 | Langberg et al. |
| 2005/0113910 A1 | 5/2005 | Paniagua et al. |
| 2005/0137692 A1 | 6/2005 | Haug et al. |
| 2005/0137695 A1 | 6/2005 | Salahieh et al. |
| 2005/0203549 A1 | 9/2005 | Realyvasquez |
| 2005/0222678 A1 | 10/2005 | Lashinski et al. |
| 2005/0240200 A1 | 10/2005 | Bergheim |
| 2005/0267572 A1 | 12/2005 | Schoon et al. |
| 2005/0283190 A1 | 12/2005 | Huitema et al. |
| 2005/0288778 A1 | 12/2005 | Shaoulian et al. |
| 2005/0288781 A1 | 12/2005 | Moaddeb et al. |
| 2006/0009737 A1 | 1/2006 | Whiting et al. |
| 2006/0020327 A1 | 1/2006 | Lashinski et al. |
| 2006/0122633 A1 | 6/2006 | To et al. |
| 2006/0129025 A1 | 6/2006 | Levine et al. |
| 2006/0155165 A1 | 7/2006 | Vanden Hoek et al. |
| 2006/0161169 A1 | 7/2006 | Nieminen et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0195183 A1 | 8/2006 | Navia et al. |
| 2006/0241748 A1 | 10/2006 | Lee et al. |
| 2006/0282161 A1 | 12/2006 | Huynh et al. |
| 2007/0016287 A1 | 1/2007 | Cartledge et al. |
| 2007/0027533 A1 | 2/2007 | Douk |
| 2007/0038296 A1 | 2/2007 | Navia |
| 2007/0051377 A1 | 3/2007 | Douk et al. |
| 2007/0067027 A1 | 3/2007 | Moaddeb et al. |
| 2007/0073098 A1 | 3/2007 | Lenker et al. |
| 2007/0080188 A1 | 4/2007 | Spence et al. |
| 2007/0093854 A1 | 4/2007 | Kayan |
| 2007/0118215 A1 | 5/2007 | Moaddeb |
| 2007/0128132 A1 | 6/2007 | Piergallini et al. |
| 2007/0135913 A1 | 6/2007 | Moaddeb et al. |
| 2007/0142907 A1 | 6/2007 | Moaddeb et al. |
| 2007/0213812 A1 | 9/2007 | Webler et al. |
| 2007/0233239 A1 | 10/2007 | Navia et al. |
| 2007/0239272 A1 | 10/2007 | Navia et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0250161 A1 | 10/2007 | Dolan |
| 2007/0293942 A1 | 12/2007 | Mirzaee |
| 2008/0177380 A1 | 7/2008 | Starksen et al. |
| 2008/0177381 A1 | 7/2008 | Navia et al. |
| 2008/0200980 A1 | 8/2008 | Robin et al. |
| 2008/0243220 A1 | 10/2008 | Barker |
| 2008/0262513 A1 | 10/2008 | Stahler et al. |
| 2008/0262609 A1 | 10/2008 | Gross et al. |
| 2008/0306586 A1 | 12/2008 | Cartledge et al. |
| 2009/0088838 A1 | 4/2009 | Shaolian et al. |
| 2009/0118747 A1 | 5/2009 | Bettuchi et al. |
| 2009/0125098 A1 | 5/2009 | Chuter |
| 2009/0149872 A1 | 6/2009 | Gross et al. |
| 2009/0216322 A1 | 8/2009 | Le et al. |
| 2009/0222083 A1 | 9/2009 | Nguyen et al. |
| 2009/0238778 A1 | 9/2009 | Mordas et al. |
| 2009/0299470 A1 | 12/2009 | Rao et al. |
| 2010/0010616 A1 | 1/2010 | Drews et al. |
| 2010/0030014 A1 | 2/2010 | Ferrazzi |
| 2010/0063586 A1 | 3/2010 | Hasenkarn et al. |
| 2010/0121433 A1 | 5/2010 | Bolling et al. |
| 2010/0161047 A1 | 6/2010 | Cabiri |
| 2010/0185274 A1 | 7/2010 | Moaddeb et al. |
| 2010/0211166 A1 | 8/2010 | Miller et al. |
| 2010/0249920 A1 | 9/2010 | Bolling et al. |
| 2010/0266989 A1 | 10/2010 | Piergallilni et al. |
| 2010/0280605 A1 | 11/2010 | Hammer et al. |
| 2010/0286767 A1 | 11/2010 | Zipory et al. |
| 2011/0022168 A1 | 1/2011 | Cartledge |
| 2011/0027753 A1 | 2/2011 | Maurat et al. |
| 2011/0034953 A1 | 2/2011 | Milo |
| 2011/0066231 A1 | 3/2011 | Cartledge et al. |
| 2011/0093062 A1 | 4/2011 | Cartledge et al. |
| 2011/0106245 A1 | 5/2011 | Miller et al. |
| 2011/0106247 A1 | 5/2011 | Miller et al. |
| 2011/0137397 A1 | 6/2011 | Chau et al. |
| 2011/0166649 A1 | 7/2011 | Gross et al. |
| 2011/0190879 A1 | 8/2011 | Bobo et al. |
| 2011/0208298 A1 | 8/2011 | Tuval et al. |
| 2011/0224785 A1 | 9/2011 | Hacohen |
| 2011/0257728 A1 | 10/2011 | Kuehn |
| 2011/0282361 A1 | 11/2011 | Miller et al. |
| 2011/0301698 A1 | 12/2011 | Miller et al. |
| 2011/0301699 A1 | 12/2011 | Saadat |
| 2012/0022557 A1 | 1/2012 | Cabiri et al. |
| 2012/0022644 A1 | 1/2012 | Reich et al. |
| 2012/0059458 A1 | 4/2012 | Buchbinder et al. |
| 2012/0095455 A1 | 4/2012 | Rodmond et al. |

(56) References Cited

U.S. PATENT DOCUMENTS

| | | | |
|---|---|---|---|
| 2012/0123531 A1* | 5/2012 | Tsukashima | A61F 2/2448 623/2.37 |
| 2012/0136436 A1 | 5/2012 | Cabiri et al. | |
| 2012/0165930 A1 | 6/2012 | Gifford, III et al. | |
| 2012/0245604 A1 | 9/2012 | Tegzes | |
| 2012/0310330 A1 | 12/2012 | Buchbinder et al. | |
| 2013/0087598 A1 | 4/2013 | Surti | |
| 2013/0116780 A1 | 5/2013 | Miller et al. | |
| 2013/0166022 A1 | 6/2013 | Conklin | |
| 2013/0204361 A1 | 8/2013 | Adams et al. | |
| 2013/0226289 A1* | 8/2013 | Shaolian | A61F 2/2466 623/2.11 |
| 2013/0226290 A1* | 8/2013 | Yellin | A61F 2/2448 623/2.11 |
| 2013/0282114 A1 | 10/2013 | Schweich, Jr. et al. | |
| 2013/0289718 A1 | 10/2013 | Tsukashima et al. | |
| 2013/0289720 A1 | 10/2013 | Dobrilovic | |
| 2013/0304197 A1 | 11/2013 | Buchbinder et al. | |
| 2014/0005778 A1 | 1/2014 | Buchbinder et al. | |
| 2014/0046433 A1 | 2/2014 | Kovalsky | |
| 2014/0058505 A1 | 2/2014 | Bielefeld | |
| 2014/0114407 A1 | 4/2014 | Rajamannan | |
| 2015/0173897 A1 | 6/2015 | Raanani et al. | |
| 2015/0173987 A1 | 6/2015 | Albinmousa et al. | |
| 2015/0351903 A1 | 12/2015 | Morriss et al. | |
| 2016/0022419 A1 | 1/2016 | Yellin et al. | |
| 2016/0038286 A1 | 2/2016 | Yellin et al. | |
| 2016/0089235 A1 | 3/2016 | Yellin | |
| 2016/0106420 A1 | 4/2016 | Foerster et al. | |
| 2016/0120642 A1 | 5/2016 | Shaolian et al. | |
| 2016/0120645 A1 | 5/2016 | Alon | |
| 2017/0042670 A1 | 2/2017 | Shaolian et al. | |
| 2017/0231763 A1 | 8/2017 | Yellin | |
| 2018/0042723 A1 | 2/2018 | Yellin et al. | |

FOREIGN PATENT DOCUMENTS

| | | |
|---|---|---|
| EP | 2928538 A1 | 10/2015 |
| EP | 2967700 A | 1/2016 |
| EP | 3213715 A1 | 9/2017 |
| KR | 10-2004-0095482 A | 11/2004 |
| RU | 125062 U1 | 2/2013 |
| WO | 1990009153 A1 | 2/1993 |
| WO | 2003017874 A1 | 3/2003 |
| WO | 2003047467 A1 | 6/2003 |
| WO | 2005046488 A2 | 5/2005 |
| WO | 2009052427 A1 | 4/2009 |
| WO | 2009120764 A2 | 10/2009 |
| WO | 2010004546 A1 | 1/2010 |
| WO | 2010085659 A1 | 7/2010 |
| WO | 2011011443 A2 | 1/2011 |
| WO | 2011097355 A2 | 8/2011 |
| WO | 2012004679 A2 | 1/2012 |
| WO | 2012019052 A2 | 2/2012 |
| WO | 2012063228 A1 | 5/2012 |
| WO | 2012095159 A2 | 7/2012 |
| WO | 2012106354 A1 | 8/2012 |
| WO | 2012167095 A2 | 12/2012 |
| WO | 2013095816 A1 | 6/2013 |
| WO | 2013128436 A1 | 9/2013 |
| WO | 2013130641 A1 | 9/2013 |
| WO | 2013175468 A2 | 11/2013 |
| WO | 2014145399 A1 | 9/2014 |
| WO | 2014189509 A1 | 11/2014 |
| WO | 2014190329 A1 | 11/2014 |
| WO | 2014210600 A2 | 12/2014 |
| WO | 2015132668 A1 | 9/2015 |
| WO | 2018035118 A1 | 2/2018 |

OTHER PUBLICATIONS

European Search Report in EP 17155803.4 dated Aug. 9, 2017.
International Search Report and Written Opinion for PCT/US2014/044920 dated Dec. 24, 2014.
International Search Report and Written Opinion for PCT/US2011/046659 dated Jun. 4, 2012.
International Search Report and Written Opinion for PCT/US2012/040481 dated Dec. 6, 2012.
International Search Report and Written Opinion for PCT/US2013/042275 dated Feb. 20, 2014.
International Search Report and Written Opinion for PCT/US2013/073552 dated Mar. 6, 2014.
International Search Report and Written Opinion for PCT/US2014/039545 dated Oct. 22, 2014.
International Search Report and Written Opinion for PCT/US2014/030163 dated Aug. 27, 2014.
International Search Report and Written Opinion for PCT/US2013/058102 dated Apr. 21, 2014.
International Search Report and Written Opinion for PCT/US2013/028065 dated Jun. 27, 2013.
Lendlein et al., Biodegradable, Elastic Shape-Memory Polymers for Potential Biomedical Applications, May 31, 2002, Science 296:1673-1676.
Supplemental European Search Report and Written Opinion for EP 12793292.9 dated Dec. 1, 2014.
Supplemental European Search Report and Written Opinion for EP 14762806.9 dated Jul. 29, 2016.
International Search Report and Written Opinion for PCT/US2017/046933 dated Dec. 21, 2017.
Communication pursuant to Article 94(3) EPC for EP 14801009.3 dated Sep. 27, 2018.
Supplementary Partial European Search Report for EP 13755441 dated Nov. 3, 2015.
International Search Report and Written Opinion for PCT2019/064289 dated Feb. 5, 2020.
17841988.3, Extended European Search Report, dated Dec. 16, 2019 ,8 pages.
PCT/US2017/046933, International Search Report and Written Opinion, dated Dec. 21, 2017 ,10 pages.

* cited by examiner

DEVICES AND METHODS FOR THE TREATMENT OF HEART VALVE INSUFFICIENCIES

CROSS-REFERENCED TO RELATED APPLICATIONS

The present application claims benefit of priority under 35 U.S.C. 119(e) to the filing date of U.S. Provisional Patent Application 62/375,079 filed Aug. 15, 2016, entitled, "DEVICES AND METHODS FOR THE TREATMENT OF HEART VALVE INSUFFICIENCIES," the contents of which is incorporated herein by reference in their entirety.

BACKGROUND

The present disclosure is generally related to a device for minimally invasive treatment of human tricuspid valve regurgitation.

Tricuspid valve regurgitation is a condition evidenced by leakiness of the tricuspid valve, which is the valve between the upper and lower chambers of the right side of the heart. An individual exhibiting tricuspid valve regurgitation will have blood leak backwards through the tricuspid valve each time the right ventricle contracts. More particularly, when the right ventricle contracts to pump blood toward the lungs, some of the blood leaks backward into the right atrium. This increases the volume of blood in the atrium, which can cause the right atrium to enlarge. Enlargement of the right atrium can result in a change in the pressure in both the nearby heart chambers and adjacent blood vessels.

Functional tricuspid valve regurgitation is the most common type of valve pathology and is usually associated with mitral valve disease. Currently, the majority of patients with both mitral valve disease and tricuspid valve regurgitation receive surgical treatment for the mitral valve only. Tricuspid valve regurgitation is most often under-diagnosed and/or ignored. Asymptotic dilation of the tricuspid annulus may benefit from repair independent of regurgitation. Without treatment for tricuspid dilation, mitral valve disease can lead to biventricular failure and even death.

Thus, a device and method for a minimally invasive treatment of human tricuspid valve regurgitation is needed.

SUMMARY

An embodiment of a device for minimally invasive medical treatment comprising: a hollow tube comprising: a first end; a second end; an exterior having a plurality of cutouts, wherein the cutouts allow the hollow tube to be flexible; at least one snap mechanism configured to connect the first end and the second end together; and one or more anchors configured to extend outward from the exterior.

BRIEF DESCRIPTION OF THE DRAWINGS

Aspects, features, benefits and advantages of the embodiments described herein will be apparent with regard to the following description, appended claims, and accompanying drawings where:

DETAILED DESCRIPTION

Figure 1:
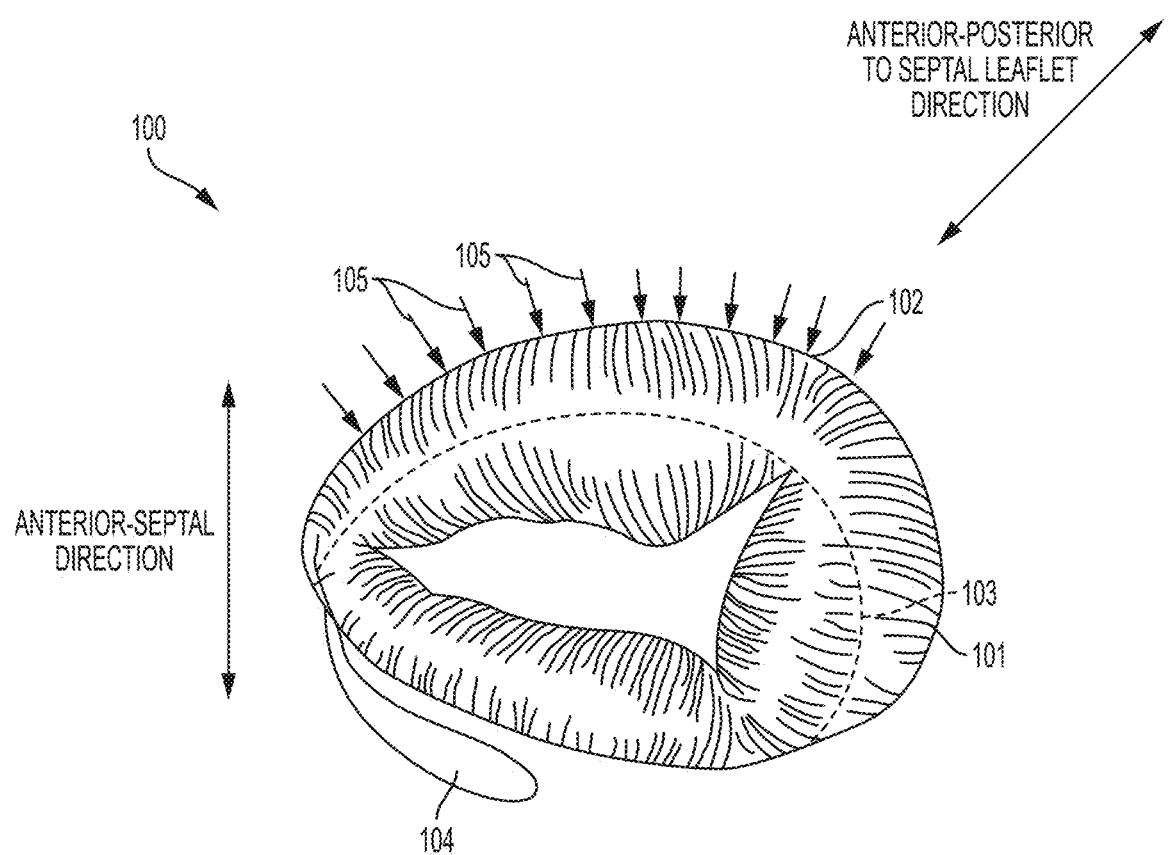
FIG. 1 depicts an illustrated tricuspid valve in normal and dilated conditions.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

As discussed herein, the existing treatment for tricuspid valve regurgitation is invasive and potentially dangerous. For example, current treatment may include repair methods such as DeVega Repair and utilization of annuloplasty rings or tricuspid rings that require open heart surgery. Open heart surgery may introduce several comorbidities in addition to any existing conditions. Thus, many patients who suffer from tricuspid valve regurgitation may not be appropriate candidates for open heart surgery, and would therefore greatly benefit from a new device and/or method for percutaneous or minimally invasive treatment of tricuspid valve regurgitation.

An implant and delivery system for introduction of a semi-rigid ring for treatment of tricuspid valve regurgitation includes a tricuspid annuloplasty ring comprising an outer hollow member with a plurality of segments. In a further embodiment, segments may be adjustable and may cooperate with one another in order to change the outer hollow member from an elongated insertion shaped geometry to an annular operable shaped geometry. The tricuspid annuloplasty ring may include one or more zones comprising internal anchor members located at least partially within the outer hollow member. In one non-limiting embodiment, the tricuspid annuloplasty ring may include up to four different anchor zones, which are further discussed herein. In an embodiment, the internal anchor members may be configured to emerge sequentially from windows (i.e., openings) along the hollow tube, thereby engaging the tissue of the tricuspid valve annulus under treatment, potentially in a predetermined sequence.

Disclosed herein are various embodiments related to minimally invasive or percutaneous trans-catheter delivery of a tricuspid ring. In addition, an embodiment may comprise methods for reducing or adjusting the dimension between the anterior and septal leaflets and/or reducing or adjusting the dimension between the anteroposterior commissure to septal leaflet, thereby minimizing or eliminating the issue of tricuspid valve regurgitation.

The illustrated example embodiments will be best understood by reference to the figures. The following description is intended only by way of example, and simply illustrates certain example embodiments.

Referring to FIG. 1, a perspective view of a tricuspid valve 100, as it relates to various embodiments discussed herein, is shown. As shown, in an embodiment, the tricuspid valve 100 may have an anterior-septal direction and an anterior-posterior to septal leaflet direction. Additionally, FIG. 1 illustrates an outline of a normal sized annulus 101, a dilated annulus 102, a desired shape of a tricuspid ring 103, and an Atrioventricular (AV) node 104. FIG. 1 further shows the annular reduction directions (i.e., the plurality of arrows 105) that may be required to reduce tricuspid valve regurgitation.

As would be understood by one skilled in the art, the AV node 104 is a part of the electrical conduction system of the heart that coordinates the top of the heart. The AV node 104 is an area of specialized tissue between the atria and the ventricles of the heart, specifically in the posteroinferior region of the interatrial septum near the opening of the coronary sinus, which conducts the normal electrical impulse from the atria to the ventricles. Puncturing or introducing any impulse into this node causes adverse effects such as Arrhythmia, irregular heart rhythm, and, in the worst, case heart failure. Therefore, in an embodiment, the design of a tricuspid ring may not include anchors in the segment of the ring that will be located adjacent to the AV node.

Figure 2:
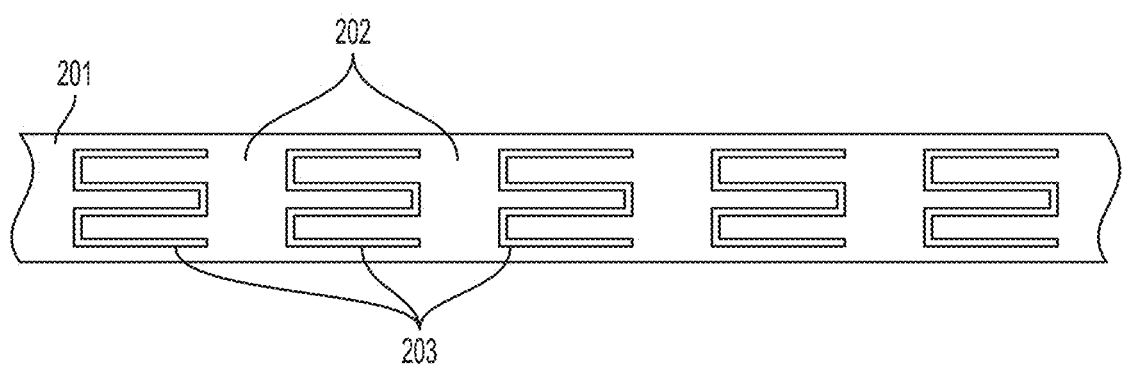
FIG. 2 depicts an illustrated pattern cut into a hollow tube, which is used to form a tricuspid ring.
Figure 3:
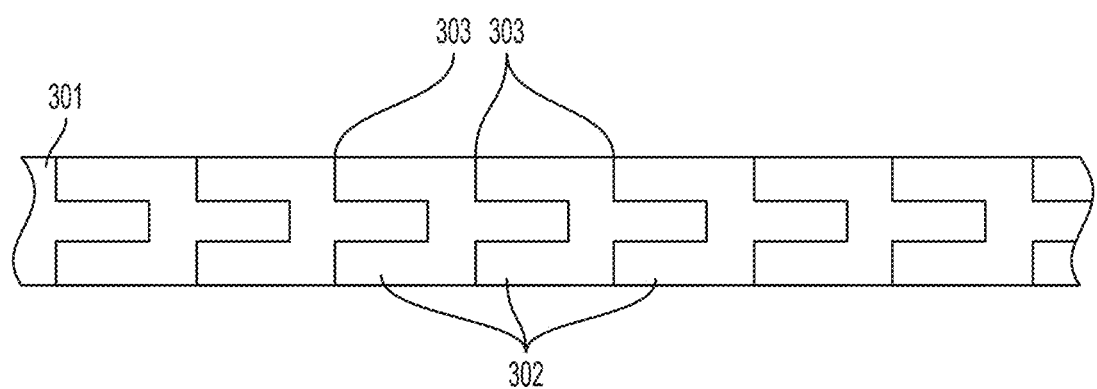
FIG. 3 depicts another illustrated pattern cut into a hollow tube, which is used to form a tricuspid ring.
Figure 4:
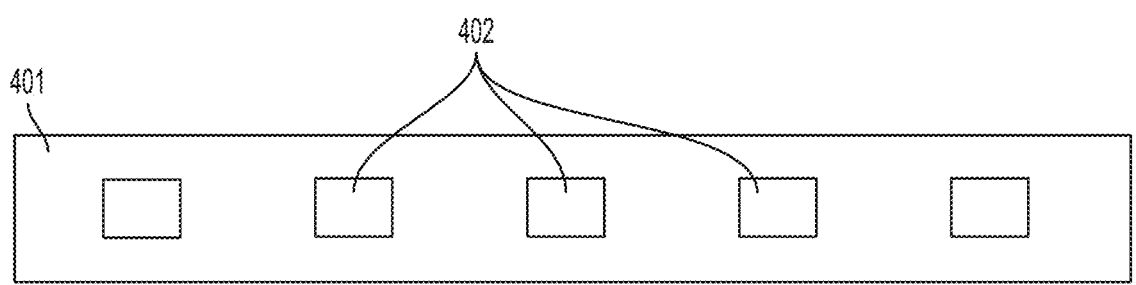
FIG. 4 depicts the back side of the hollow tube and the pattern of the cuts for anchor deployment windows.

In FIGS. 2 and 3, a perspective view of an illustrative embodiment may include a hollow tube 201/301, which may be made of various materials (e.g., a shape memory hypotube (nickel titanium (Ni—Ti) super elastic alloy)) cut to form a plurality of segments 202/302. In one embodiment, the cuts 203/303 in the hollow tube may allow for the tube to be used as an outer tube of a segmented tricuspid annuloplasty ring. Additionally, FIG. 4 shows an illustrative schematic diagram further detailing the cutting pattern used for laser processing (e.g., the cutting of windows 402 through which anchors (not shown) may be deployed) of the hypo tube 401 as illustrated in FIGS. 2 and 3.

Figure 5:
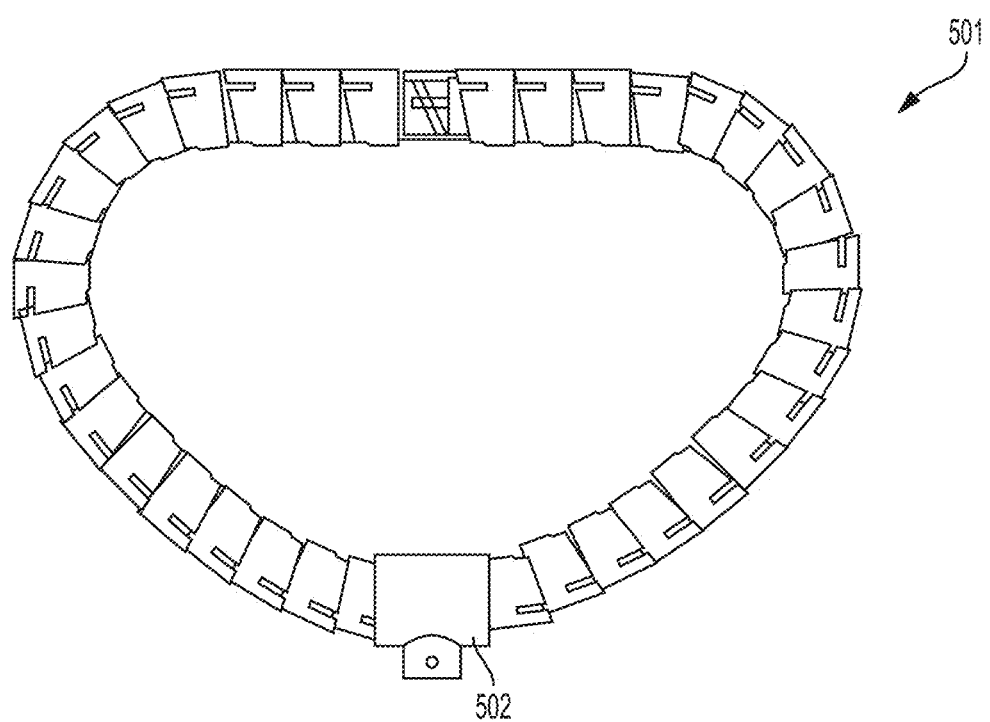
FIG. 5 depicts an illustrated shape of a tricuspid ring.

In an embodiment, as shown by the schematic diagram in FIG. 5, the shape of the memory hypotube 501, as discussed and shown in FIGS. 2 and 3, may have an operable geometry. For example, the hypotube may be annular and/or D shaped (as shown in FIG. 5). Furthermore, an embodiment may, as shown, comprise a delivery system interface point 502.

Figure 6:
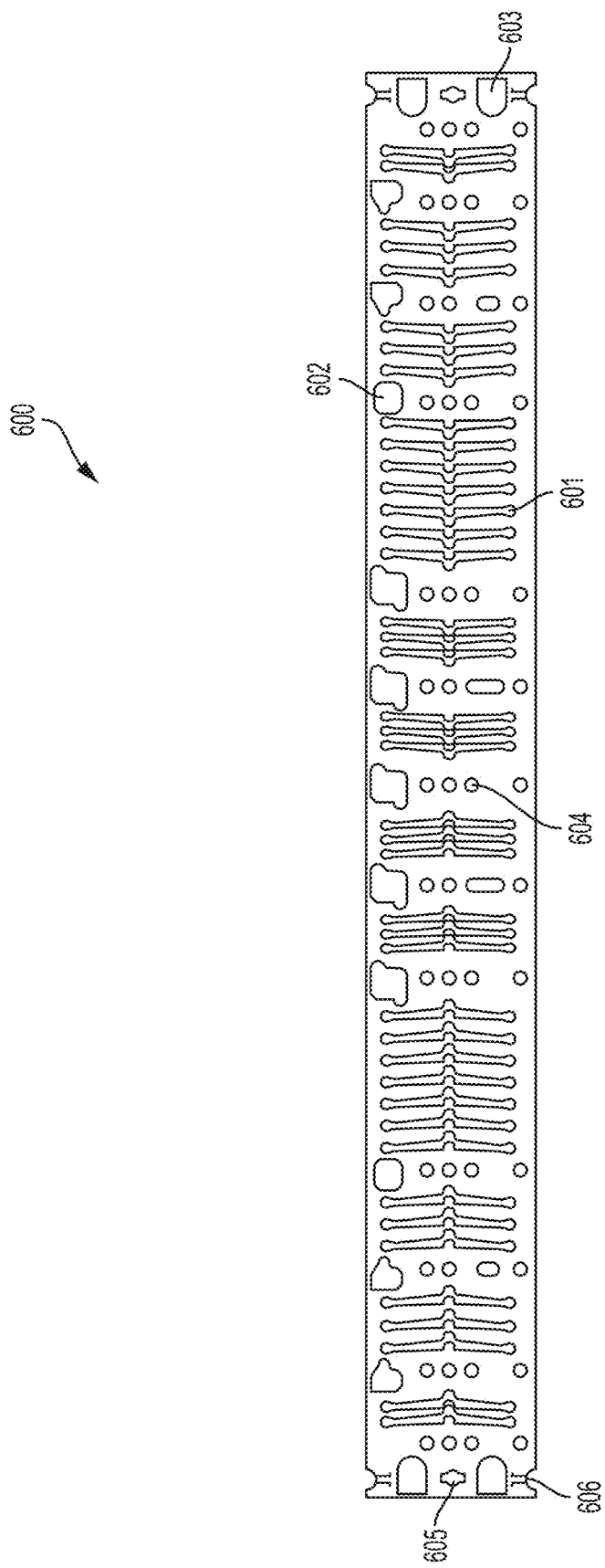
FIG. 6 depicts an illustrated schematic laser cut pattern.

Referring now to FIG. 6, a schematic laser cut pattern 600 for use in laser processing is shown. In one embodiment, the laser cut pattern 100 may integrate a plurality of segments (e.g., the windows for the anchors and the specific attachment holes for additional members. In one embodiment, a closing feature(s) may utilize the specific attachment holes in order to secure a connection and close the tricuspid ring. Thus, as shown in FIG. 6, an illustrative embodiment may include one or more laser cut patterns 600, one or more laser cut slots for flexibility 601, one or more windows for anchors 602, one or more windows for sutures 603, one or more holes for fabric attachment and fluorinated ethylene propylene (FEP) attachment 604, one or more holes for a suture pin 605, and one or more snap features for the suture pin 606.

Fluorinated ethylene propylene or FEP is a copolymer of hexafluoropropylene and tetrafluoroethylene. It differs from polytetrafluoroethylene resins in that it is melt-processable using conventional injection molding and screw extrusion techniques. Moreover, it has a very low coefficient of friction and thus, in an embodiment, may make an exceptional material to serve as an anchor track and/or anchor the assemblies within the laser cut Ni—Ti rings. FEP provides various benefits over current methods, such require a significant pulling force to retrieve a metal end of a metal ring, particularly one that has a bend radius, after deployment from a catheter. In contrast, an embodiment may utilize an FEP tube that is laser cut and allows easy sliding of the anchor assembly within the laser cut Ni—Ti ring.

FEP is very similar in composition to the fluoropolymers PTFE (polytetrafluoroethylene) and PFA (perfluoroalkoxy polymer resin). FEP and PFA both share PTFE's useful properties of low friction and non-reactivity, but are more easily formable. FEP is softer than PTFE and melts at 260° C. It is also highly transparent and resistant to sunlight.

Figure 7:
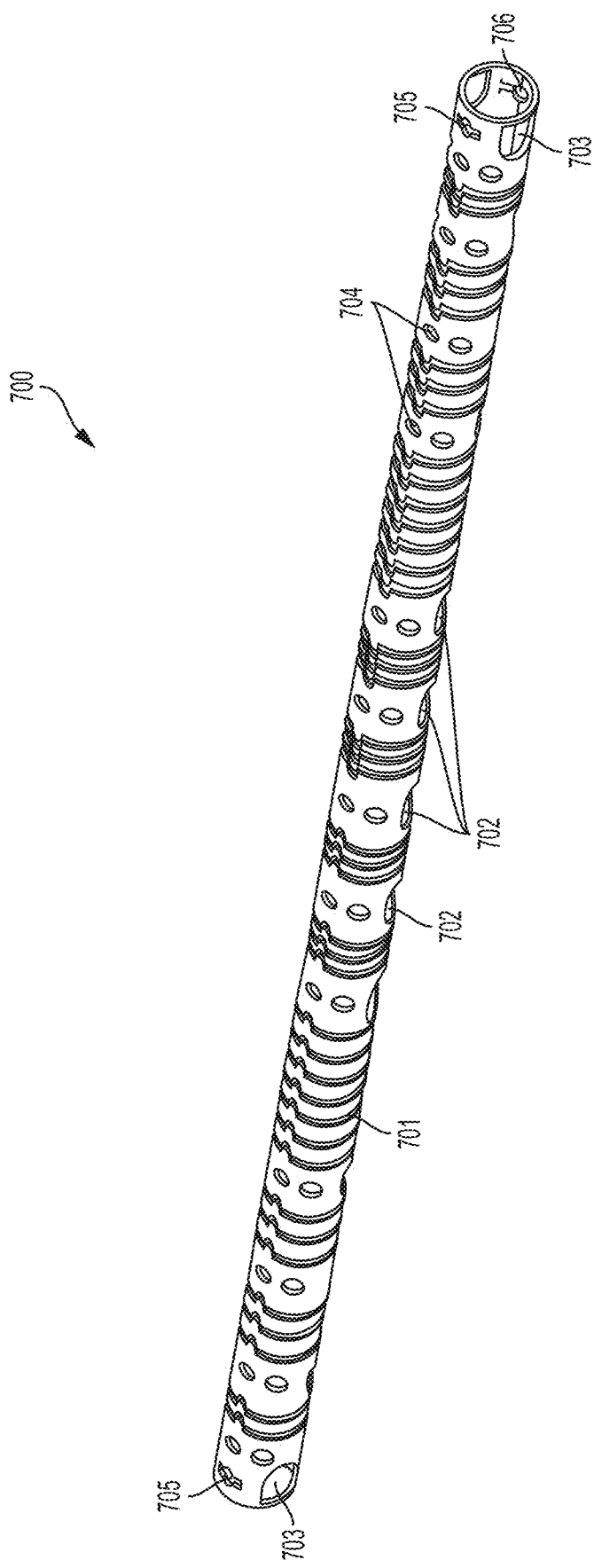
FIG. 7 depicts an illustrated schematic laser cut tube.

As shown in FIG. 7, a further embodiment may include a schematic laser cut tube 700. In one embodiment, the schematic laser cut tube 700 configuration may integrate a plurality of segments (e.g., the windows for the anchors and the specific attachment holes for additional members such as a closing feature(s) to close the tricuspid ring). Thus, as shown in FIG. 7, an illustrative embodiment may include one or more laser cut slots for flexibility 701, one or more windows for anchors 702, one or more windows for sutures 703, one or more holes for fabric and FEP attachment 704, one or more holes for a suture pin 705, and a snap feature for the suture pin 706.

Figure 8:
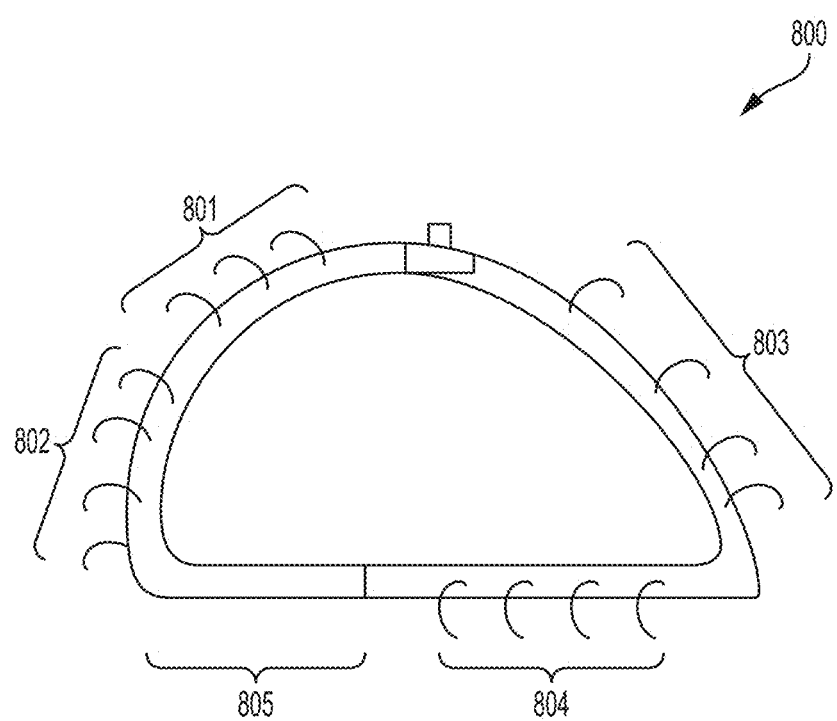
FIG. 8 depicts a perspective view of an illustrated tricuspid ring with the deployed anchors.

Referring now to FIG. 8, a perspective view of an illustrative embodiment is shown including a tricuspid annuloplasty ring 800 with four zones of internal anchors being deployed. Specifically, an embodiment may have a first anterior anchoring zone 801, a second an anterior anchoring zone 802, a posterior anchoring zone 803, a septal anchoring zone 804, and an AV node 805. In some embodiments, the AV node may comprise no anchors.

Figure 9:
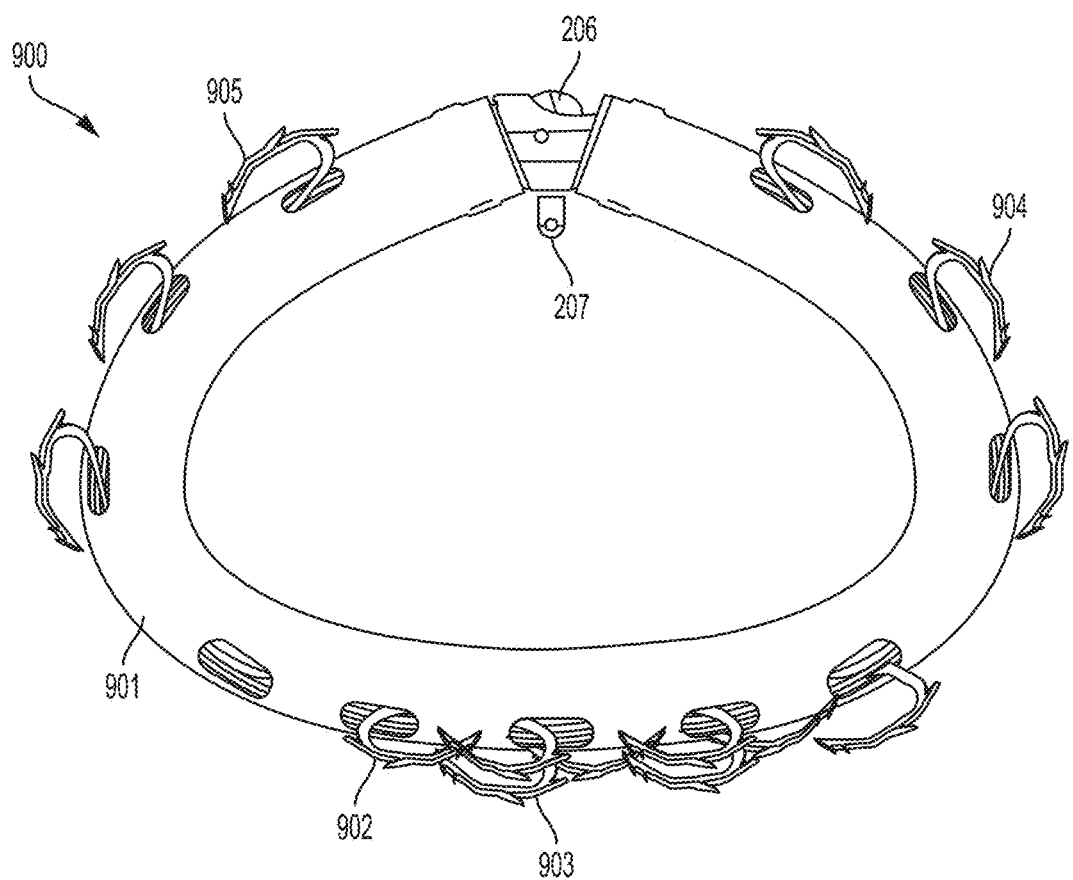
FIG. 9 depicts a perspective view of an illustrated tricuspid ring with zone distributions.

Additionally or alternatively, FIG. 9 illustrates alternative zone distributions in a tricuspid ring. In this configuration, the septal zones may overlap and thus create an improved attachment to the septal annulus. As shown in FIG. 9, an illustrative embodiment may include a tricuspid ring with four zones of anchors 900, an outer ring 901, a first septal zone 902, a second septal zone 903, a posterior zone 904, and an anterior zone 905, a snapping/closure mechanism 906, and a pivot pin attachment point 907, wherein the pivot pin attachment point attaches to a snapping mechanism of a delivery system.

Figure 10:
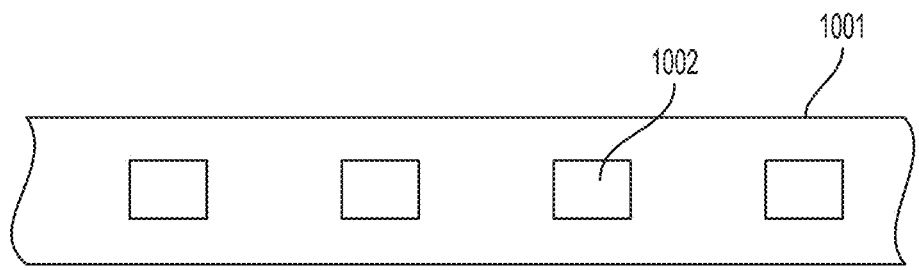
FIG. 10 depicts a perspective view of an illustrated laser cut fluorinated ethylene propylene (FEP) material.
Figure 11:
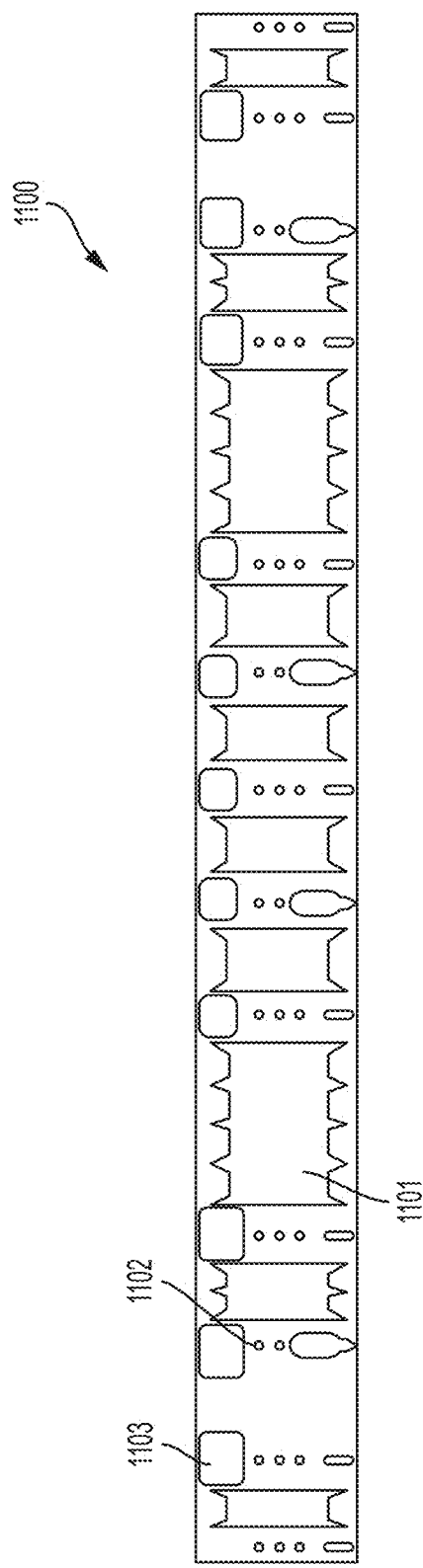
FIG. 11 depicts an illustrative laser cut pattern of an FEP tube.

Referring now to FIG. 10, a perspective view of a laser cut FEP 1001 that is used as a lining for the inside diameter of the hollow laser cut tube is shown. In one embodiment, the laser cut FEP may include laser cut anchor deployment windows 1002 that correspond to the laser cut windows on the hollow segmented tube (i.e., 700 shown in FIG. 7). Additionally, an embodiment may, as shown in FIG. 11, include a laser cut pattern 1100 for the FEP to enable it to properly line the inside diameter of the hollow laser cut tube. Moreover, as shown in FIG. 11, the laser cut pattern may include laser cut windows 1103 that correspond to laser cut windows on the hollow segmented tube, wherein both patterns allow for the flexibility of the FEP tube to bend along with the outer ring. As shown in FIG. 11, an illustrative embodiment may include a laser cut FEP 1100, a material release to allow flexibility 1101, one or more corresponding holes for sutures and coding of the FEP to the ring tube 1102, and one or more corresponding windows for the anchors 1103.

Figure 12:
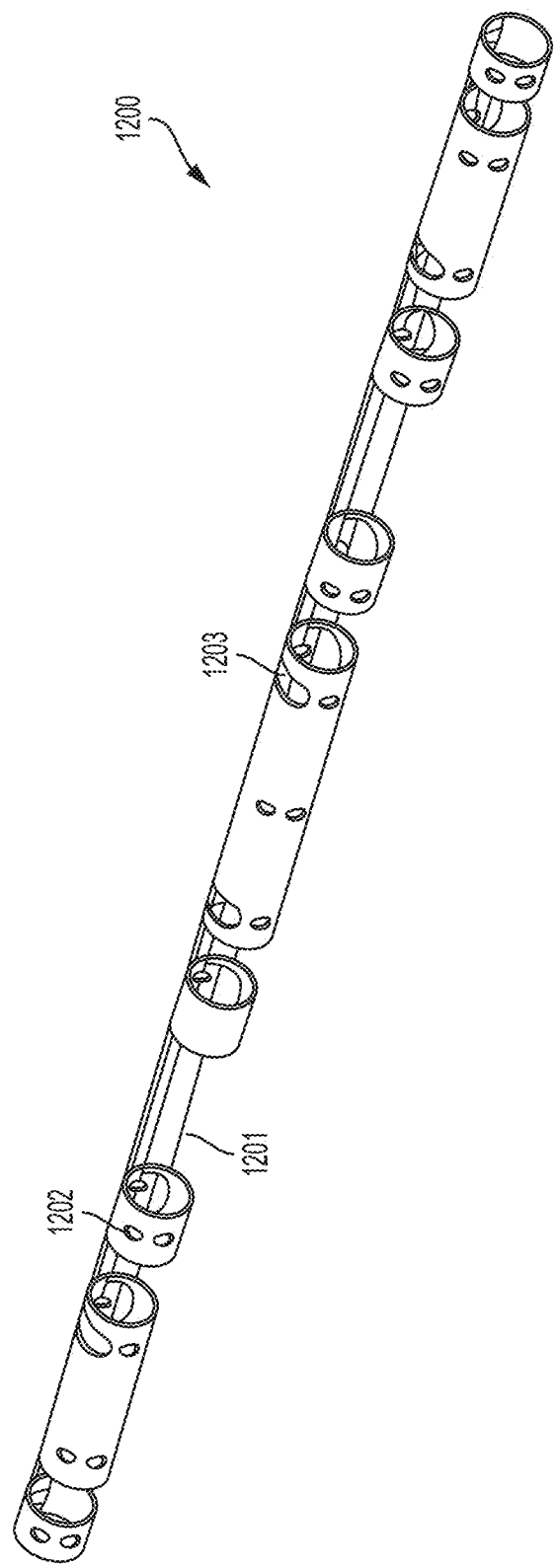
FIG. 12 depicts an illustrative laser cut FEP in a tubular configuration.

FIG. 12 shows an alternate perspective view of an embodiment including a laser cut FEP in its tubular configuration 1200. As shown, the laser cut FEP 1200 may provide a lining for the inside diameter of the hollow laser cut tube, and include one or more laser cut windows that correspond to one or more laser cut windows 1203 on the hollow segmented tube, as discussed herein. A further embodiment may have a pattern that allows the FEP tube 1200 to be flexible and bend with the outer ring, such as that shown in FIG. 12. As shown in FIG. 12, an embodiment may include a laser cut FEP 1200, a material release to allow flexibility 1201, one or more corresponding holes for sutures and coding of the FEP to the tricuspid ring tube 1202, and one or more corresponding windows 1203 for the anchors.

Figure 13:
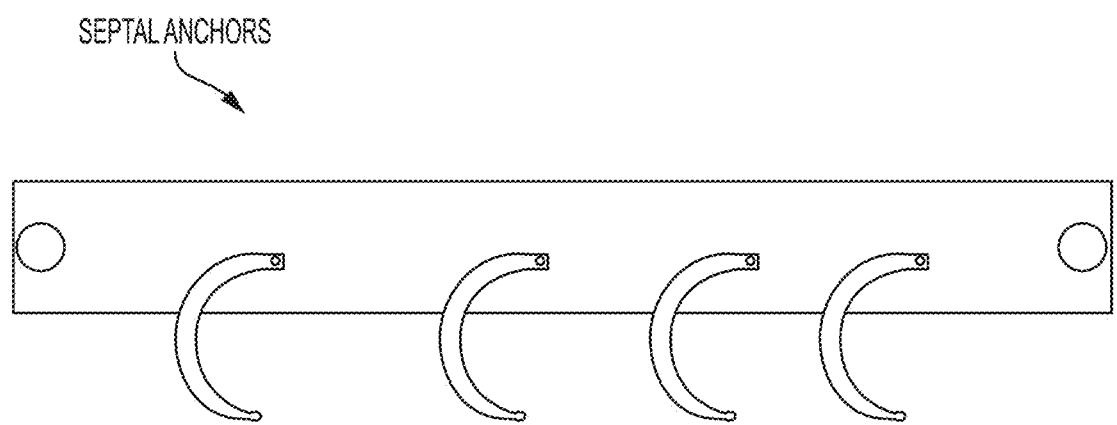
FIG. 13 depicts an illustrated geometric view of septal anchors.
Figure 14:
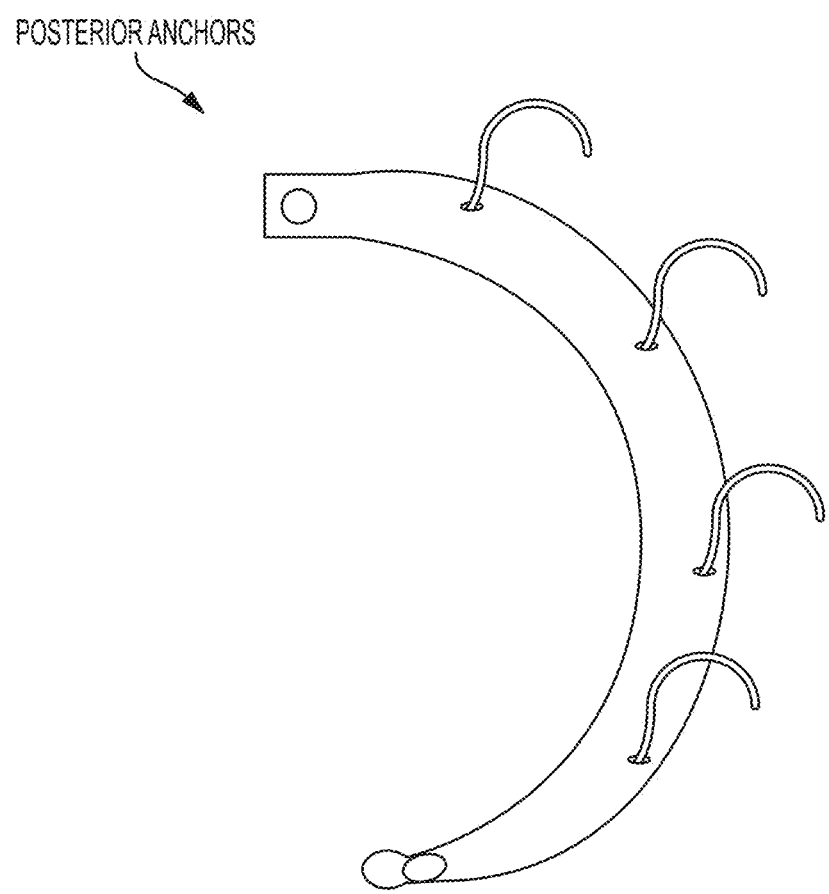
FIG. 14 depicts an illustrated geometric view of posterior anchors.
Figure 15:
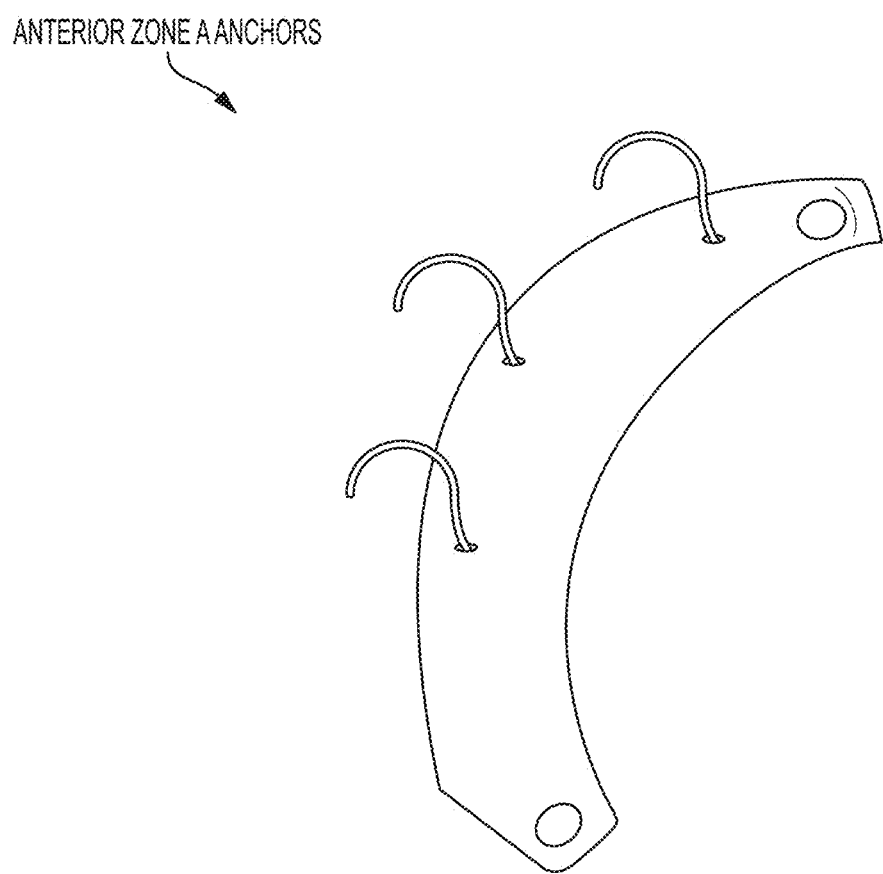
FIG. 15 depicts an illustrated geometric view of anterior anchors in zone A.
Figure 16:
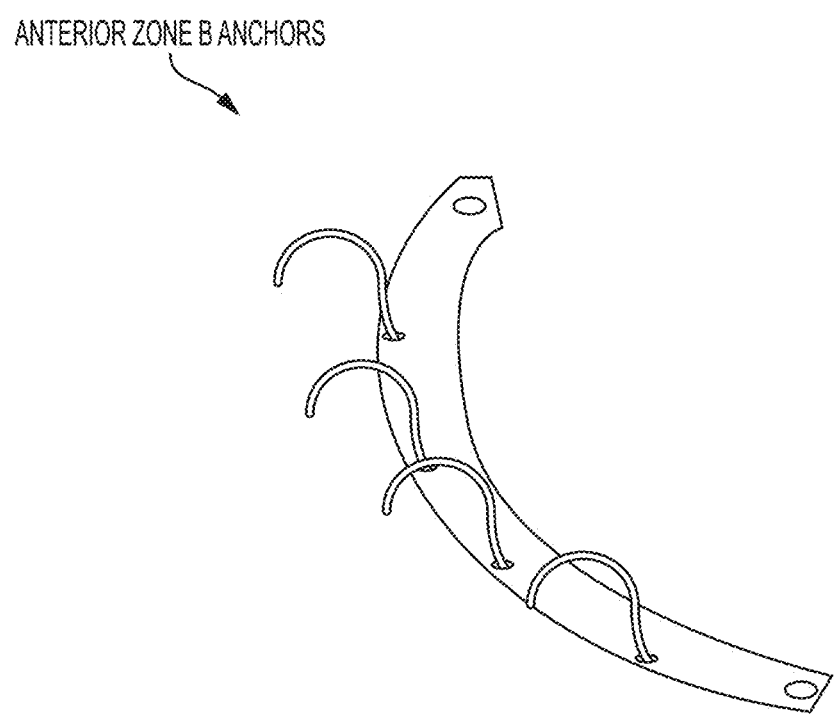
FIG. 16 depicts an illustrated geometric view of anterior anchors in zone B.

Referring to FIGS. 13-16, embodiments are shown that illustrate the geometry and view of four anchor rails. For example, FIG. 13 depicts the anchor rail for the septal zone of the tricuspid ring and FIG. 14 depicts the anchor rail for the posterior leaflet. FIGS. 15 and 16 depict two anchor rails which are each designed to anchor the tricuspid ring to the anterior section of the tricuspid valve (e.g., Zone A and Zone B of the anterior section).

Figure 17:
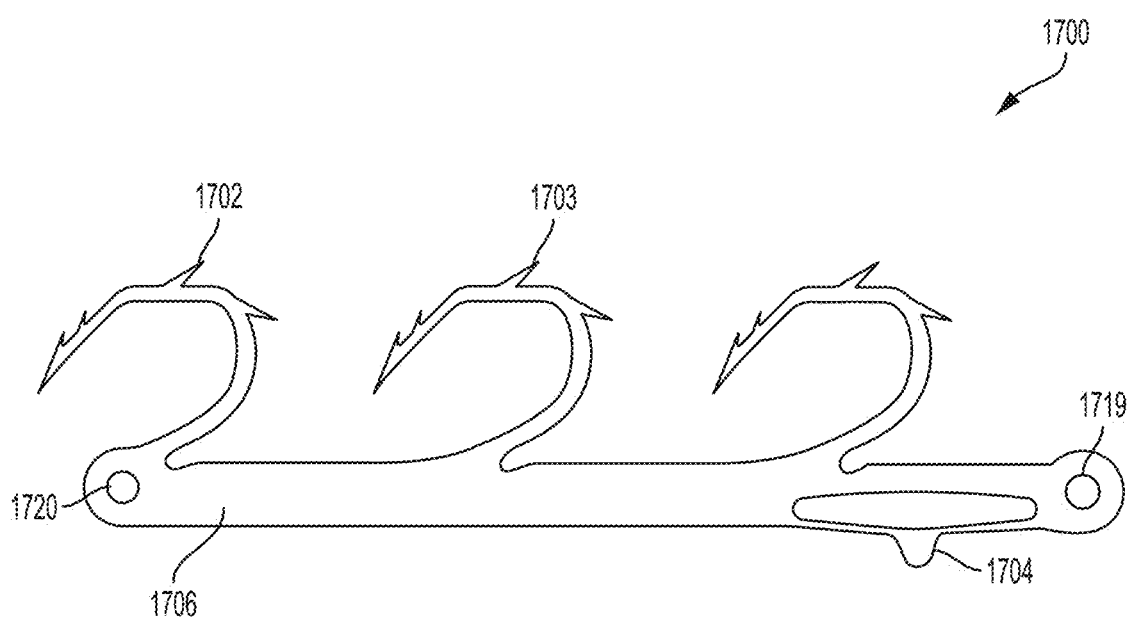
FIG. 17 depicts an illustrated laser cut pattern for a posterior and/or anterior zone.

A further embodiment, as illustrated in FIG. 17, may have an anchor system for a posterior/anterior zone. By way of non-limiting example, an illustrative embodiment, such as is shown in FIG. 17, may include an anchor zone 1700, a harpoon 1702, a harpoon barb 1703 an anchor stop (AS) feature 1704, an anchor zone rail 1706, an anchor zone deployment hole 1719, and a loading hole 1720.

As discussed herein, various embodiments may employ an anchor stop (e.g., 1704). The need for an anchor stop arises from the fact that the anchors may move after a tricuspid ring is deployed from the catheter (e.g., in linear shape) and takes on the "D" shape, as discussed herein. Specifically, the anchor assemblies that were held stationary when the ring was held in a linear position (e.g., the anchors held beneath and adjacent to the windows in the laser cut tube) may start moving and emitting prematurely from the windows because of the bend radius of the ring.

Thus, in order to combat premature deployment, which may render the ring useless and cause serious issues during the procedure, an embodiment utilizes the anchor stops to hold the anchors in place until the ring has reached its final location and deployment is appropriate. Once the assembly has reached its final location, the anchor stop may be overcome when an operator pulls a suture that is connected to the anchor assembly and forces the assembly and its stopper to slide, thus deploying the anchor systems, in the method discussed herein. Generally, an anchor stop is a bump geometrical feature, or step that prevents the anchor assembly from moving when the ring is deployed out of the delivery system; however, various embodiments and configurations are discussed herein and shown in the corresponding figures.

Figure 18:
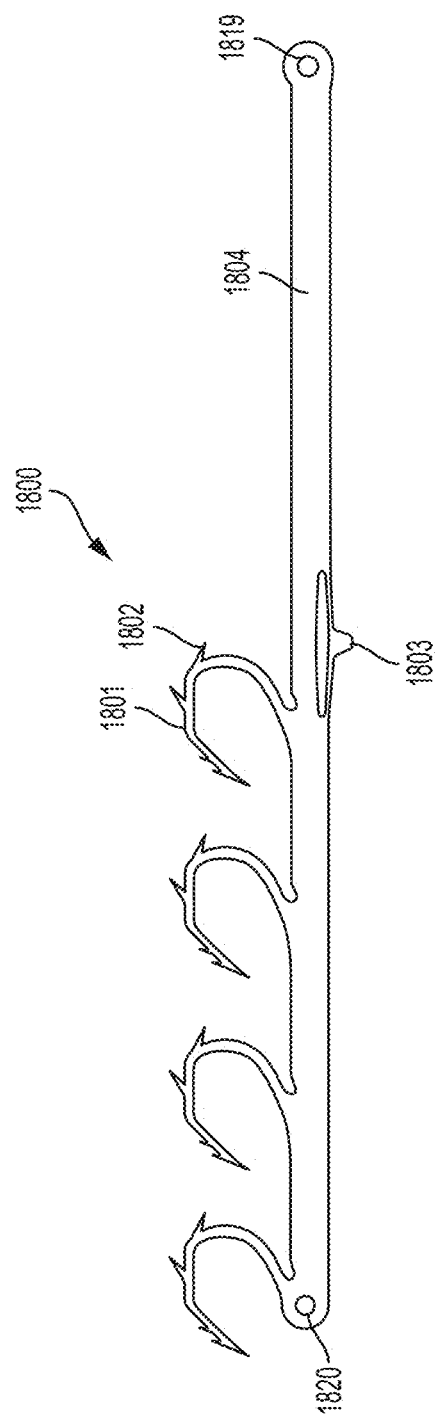
FIG. 18 depicts an illustrated laser cut pattern for a septal zone.
Figure 19:
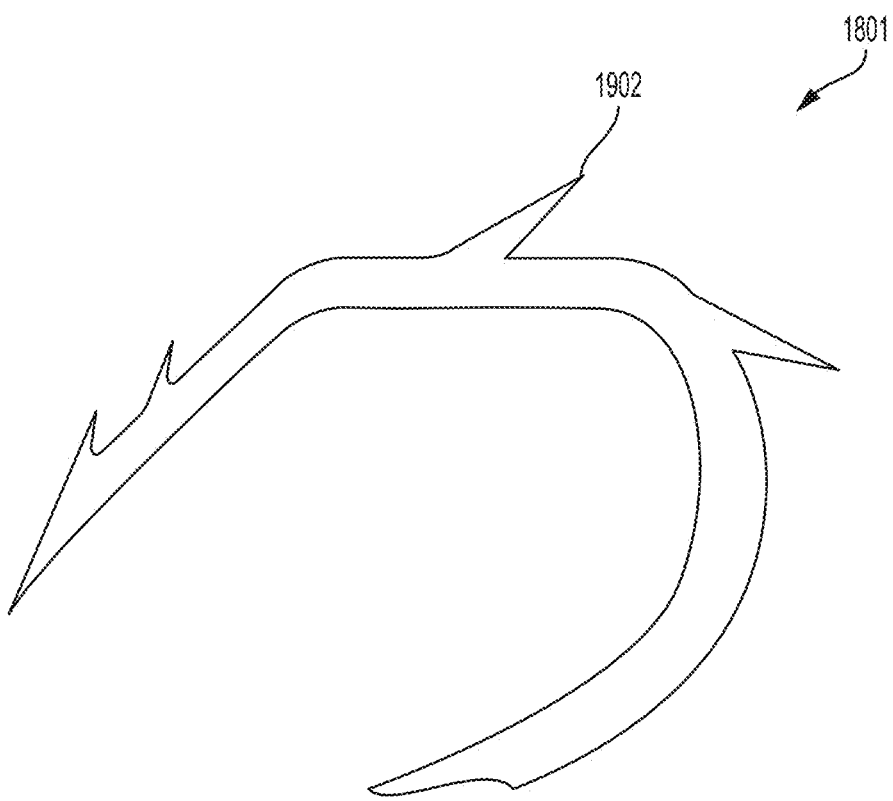
FIG. 19 depicts detail view of an illustrated harpoon.
Figure 20:
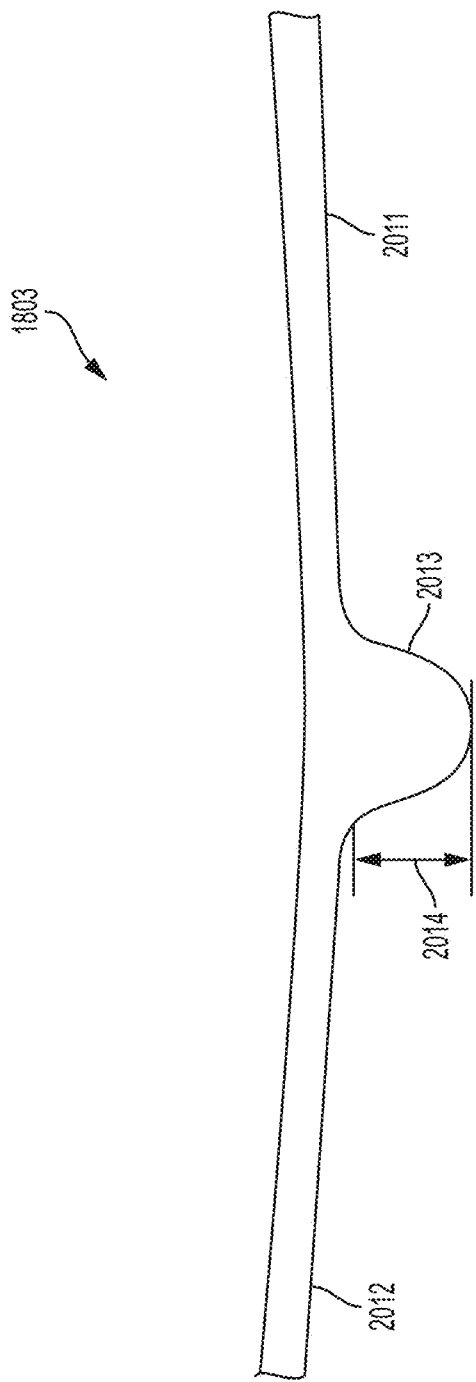
FIG. 20 depicts a detail view an illustrated anchor stop feature.

In another embodiment, illustrated in FIG. 18, a laser cut pattern may be used for a septal zone. As shown in FIG. 18, an embodiment may include an anchor zone 1800, a harpoon 1801, a harpoon barb 1802, an anchor stop (AS) feature 1803, an anchor zone rail 1804, an anchor zone deployment hole 1819, and a loading zone 1820. Additional detail regarding the harpoon 1801 is shown in FIG. 19. As illustrated by the embodiment in FIG. 19, the harpoon 1801 may have one or more harpoon barbs 1902. Additional detail regarding the anchor stop feature 1803 is shown in FIG. 20. As illustrated by the embodiment in FIG. 20, the anchor stop feature 1803 may include a first connecting strut 2011, a second connecting strut 2012, a deployment angle 2013, and an anchor stop feature height 2014.

Figure 21:
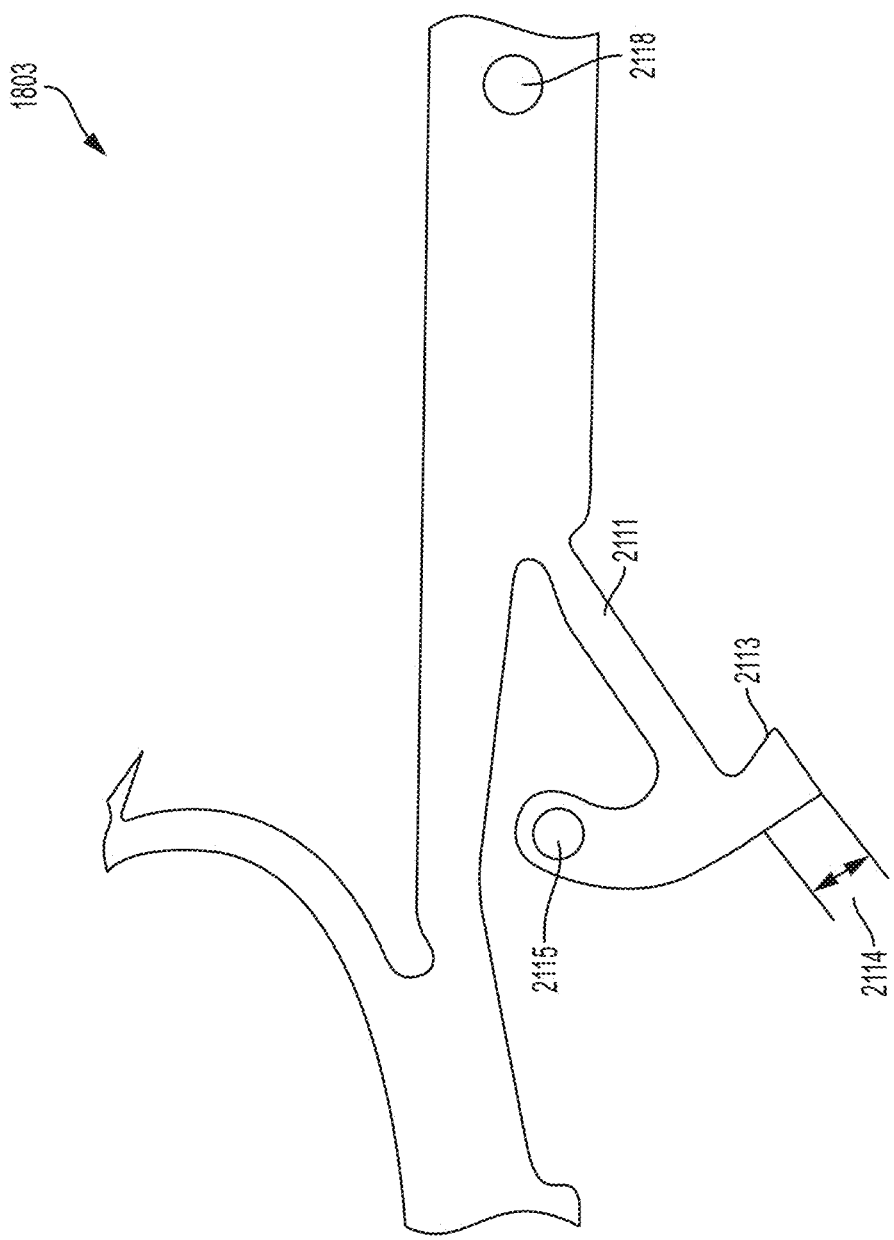
FIG. 21 depicts a detail view of another illustrated anchor stop feature

Additionally or alternatively, as shown in FIG. 21, an embodiment may include an anchor stop feature 1803 attached with one strut to an anchor zone having a negative deployment angle 2113. In a further embodiment, the anchor stop feature 1803 may include one or more deployment holes 2115. Thus, as illustrated in FIG. 21, an embodiment may include a typical anchor stop feature 1803, a first connecting strut 2111, a deployment angle 2113, an anchor stop feature height 2114, an anchor stop deployment hole 2115, and an anchor zone suture routing hole 2118.

Figure 22:
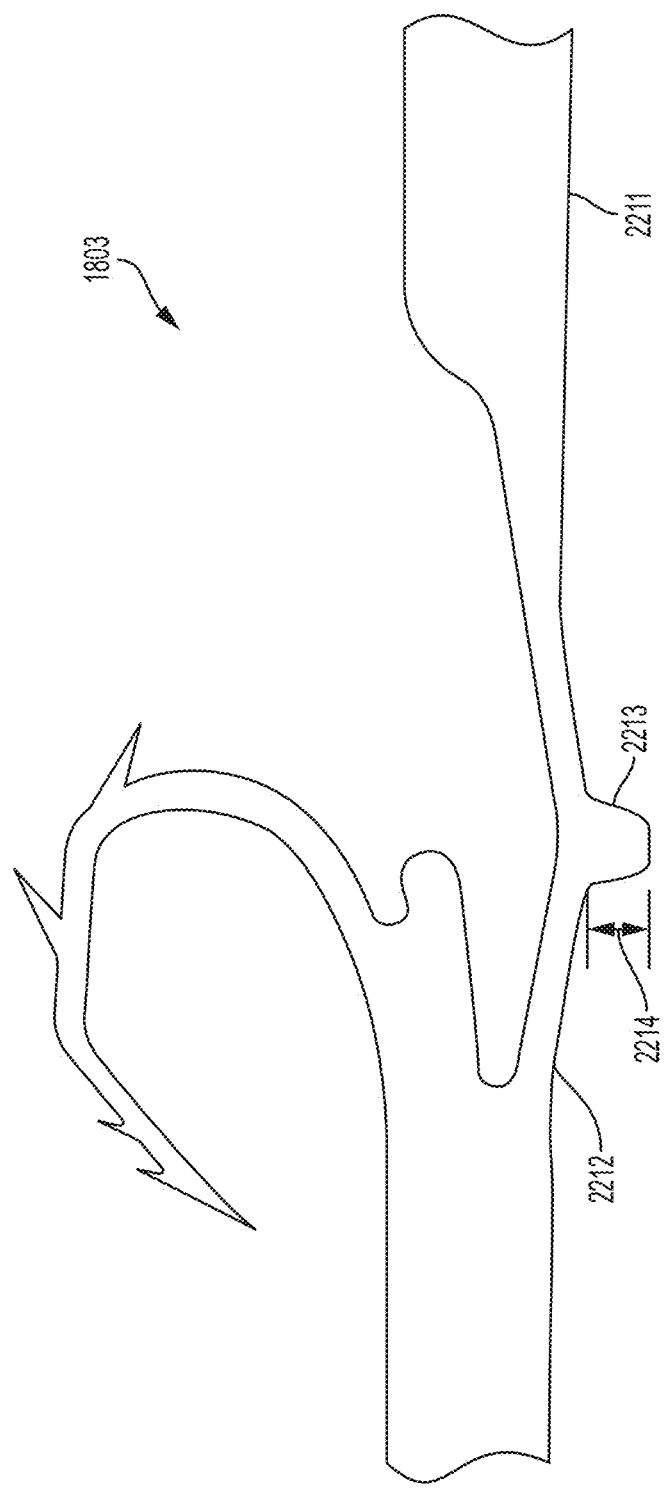
FIG. 22 depicts a detail view of another illustrated anchor stop feature.
Figure 23:
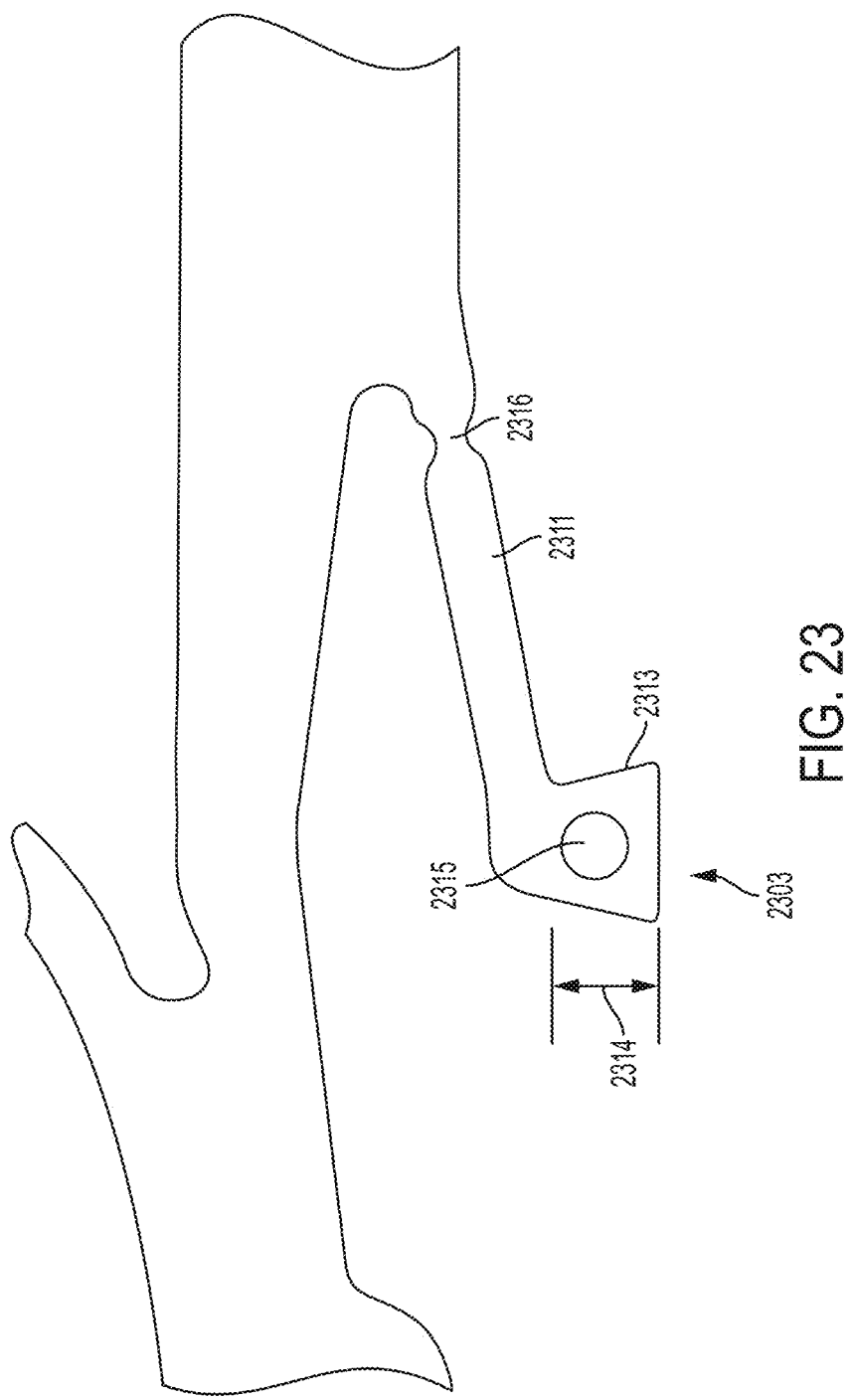
FIG. 23 depicts a detail view of another illustrated anchor stop feature.

FIG. 22 depicts another illustrative embodiment of an anchor stop feature 1803. As shown, the anchor stop feature 1803 may include a first connecting strut 2211, a second connecting strut 2212, a deployment angle 2213, and an anchor stop feature height 2214. Additionally or alternatively an embodiment, as shown in FIG. 23, may include an anchor stop feature 1803 with a weak point 2216 to direct an anchor stop disconnection at a certain point. Thus, an embodiment, as shown in FIG. 23, may include a first connecting strut 2311, a deployment angle 2313, an anchor stop feature height 2314, an anchor stop deployment hole 2315, and a weak point of the anchor stop feature strut 2316.

Figure 24:
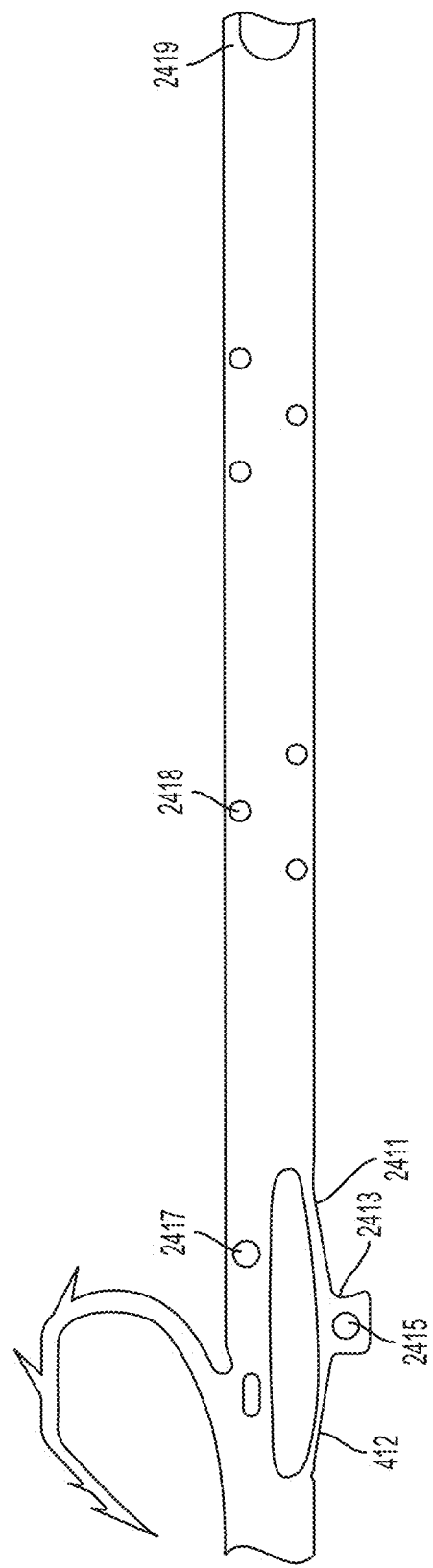
FIG. 24 depicts another illustrated anchor stop feature and an illustrated harpoon.

Referring now to FIG. 24, an embodiment may include an active anchor stop feature with activation holes 2417 on the anchor zone rail. Thus, as shown in FIG. 24, an illustrated embodiment may include a first connecting strut 2411, a deployment angle 2413, an anchor stop feature deployment hole 2415, an activation hole 2417 for transforming the suture direction from horizontal to vertical, an anchor zone suture routing hole 2418, and an anchor zone deployment hole 2419.

Figure 25:
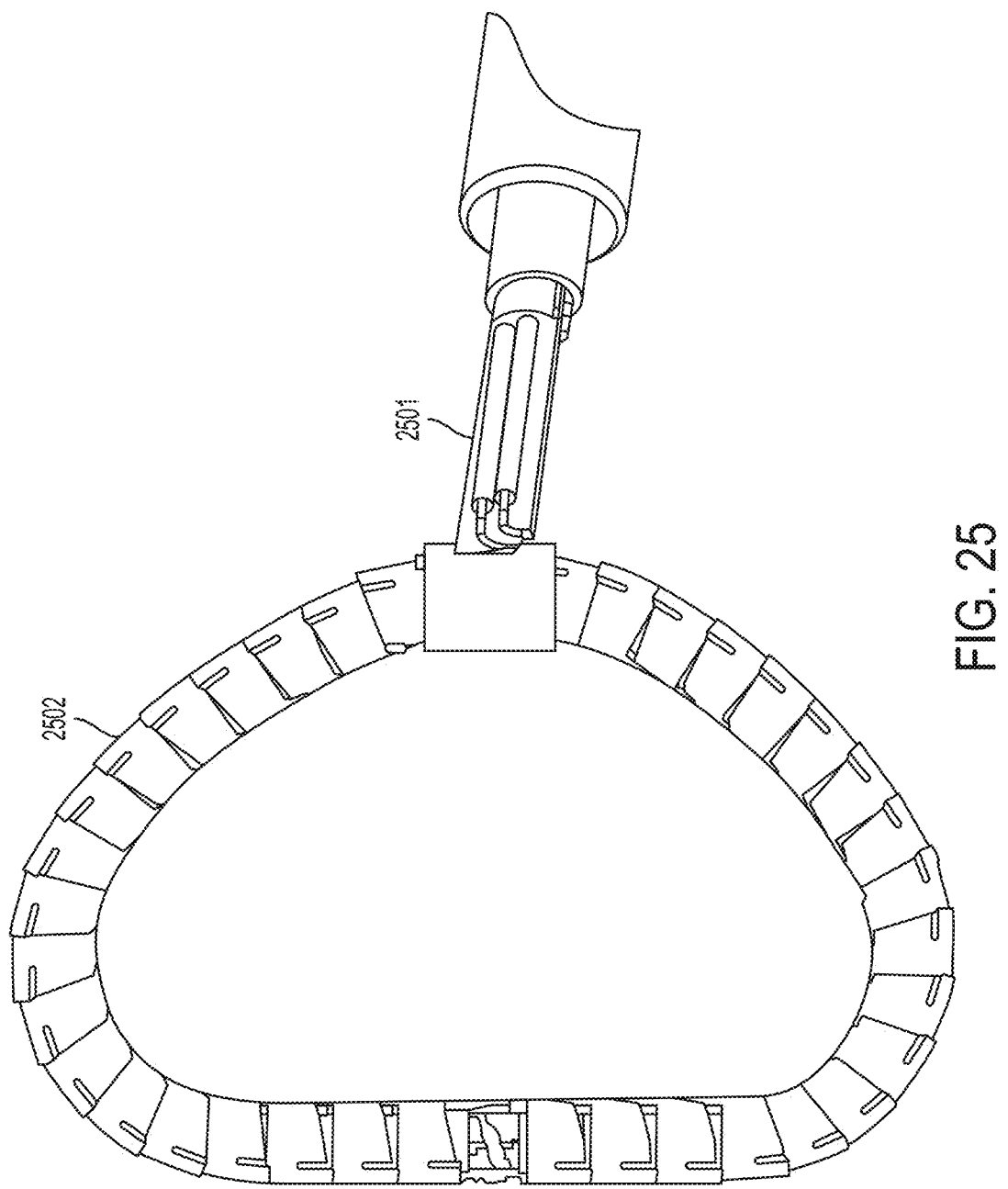
FIG. 25 depicts a perspective view of an illustrative non-deployed anchor parked adjacent to a deployment window.

As discussed herein, an embodiment may take the shape of the memory hypotube and may have an operable geometry, for example, an annular and/or D shaped geometry (as shown in FIG. 5). Referring now to FIG. 25, a perspective view of an illustrative distal end of a delivery system 2501 with an implant interface member connected to the tricuspid ring 2502 is shown.

Figure 26:
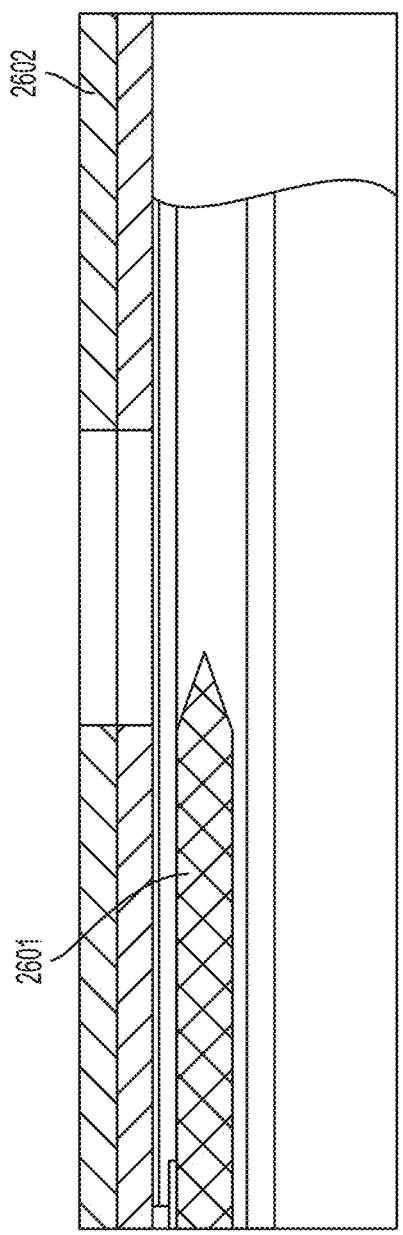
FIG. 26 depicts an illustrative view of non-deployed an anchor.
Figure 27:
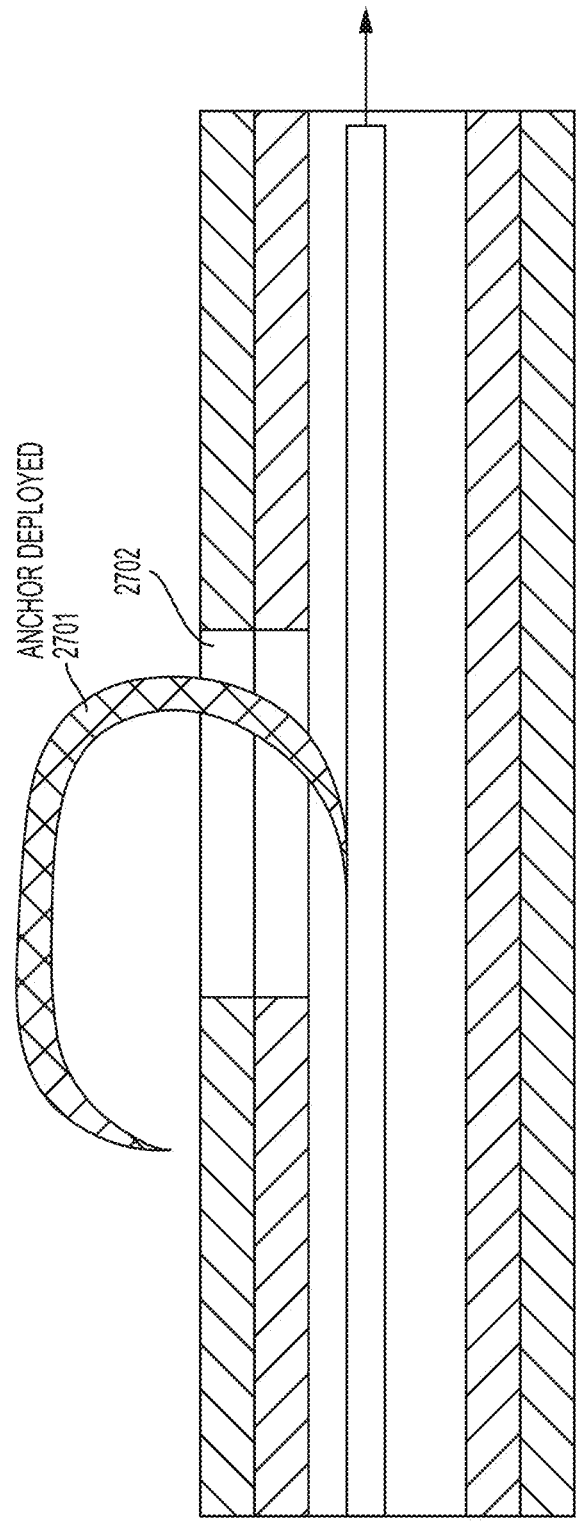
FIG. 27 depicts an illustrative view of a deployed anchor.
Figure 28:
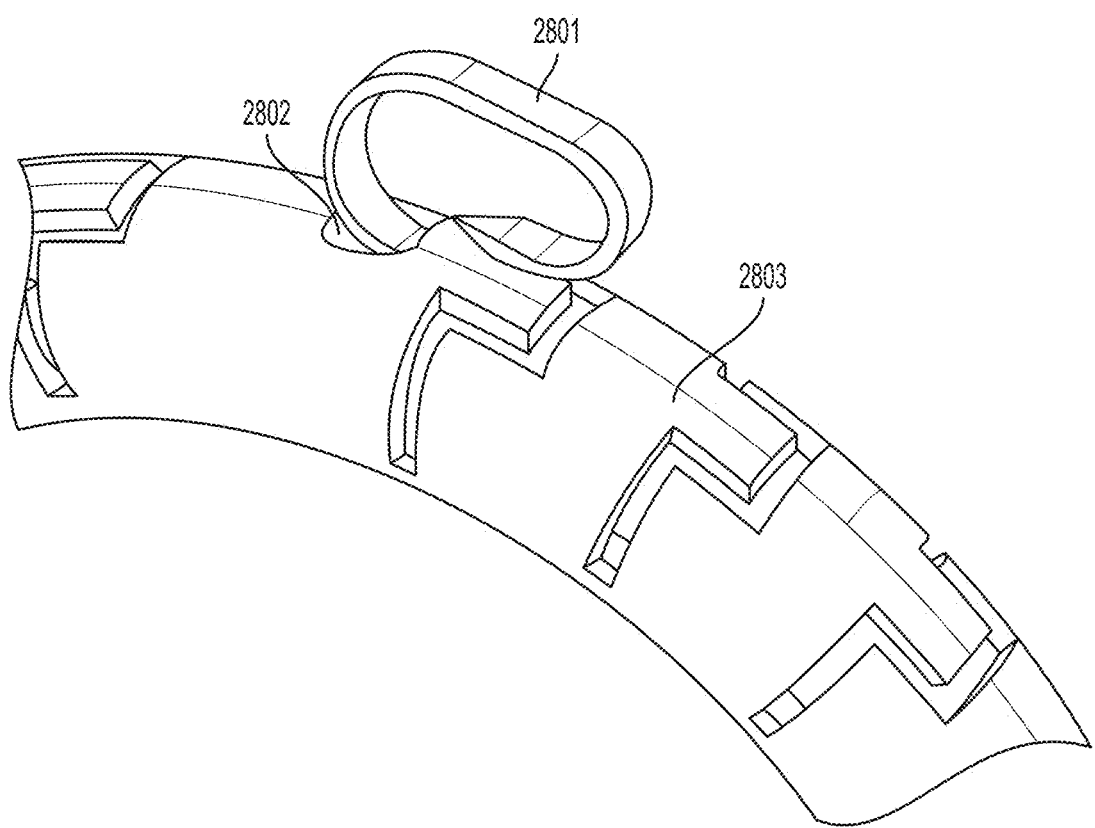
FIG. 28 depicts a detail view of a segment of the tricuspid ring with a deployed anchor.

FIGS. 26 and 27 illustrate a general view of one or more typical anchors in an initial and deployed position, respectively. In FIG. 26, the anchor 2601 is tucked within the hollow laser cut tube 2602 under its respective deployment window. In FIG. 27, a non-limiting illustration shows a deployed anchor 2701 after it has been deployed from its respective deployment window 2702. Further detail of a deployed anchor 2701 is shown in FIG. 28, which depicts a magnified view of a segment of the tricuspid ring 2803 that includes a deployment window 2802 (see also 602 of FIG. 6) and a deployment anchor 2801.

Figure 29:
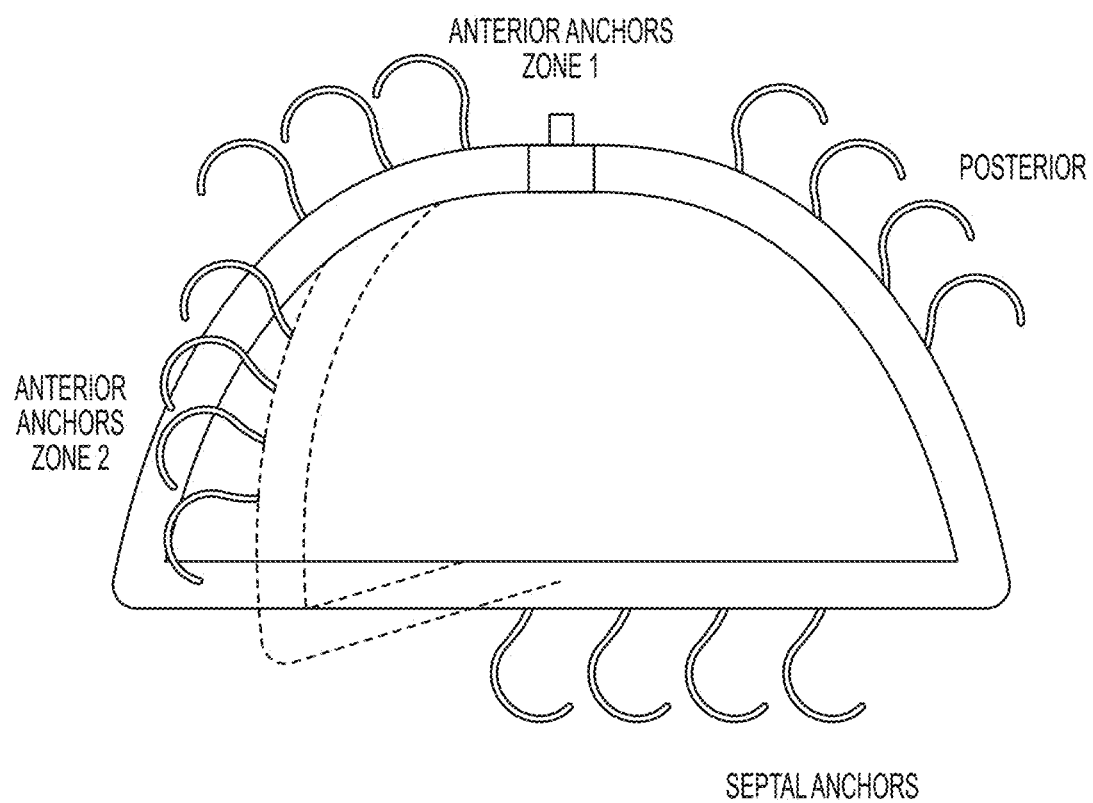
FIG. 29 depicts an illustrative initial geometry of a tricuspid ring.

Referring now to FIG. 29, an embodiment is depicted that includes an initial geometry of the tricuspid ring when deployed from the delivery system (e.g., the solid lines) and the geometry of the tricuspid ring after deployment of all anchors (e.g., the dashed lines). In some embodiments the tricuspid ring may comprise a first anterior zone, a second anterior zone, a posterior zone, and a septal zone. Thus, as shown in FIG. 29, the solid lines may depict the initially deployed geometry, while the dashed lines may depict one possible final geometry after the anterior leaflet (e.g., at zone 2) has been transferred to reduce the anterior septal height.

Figure 30:
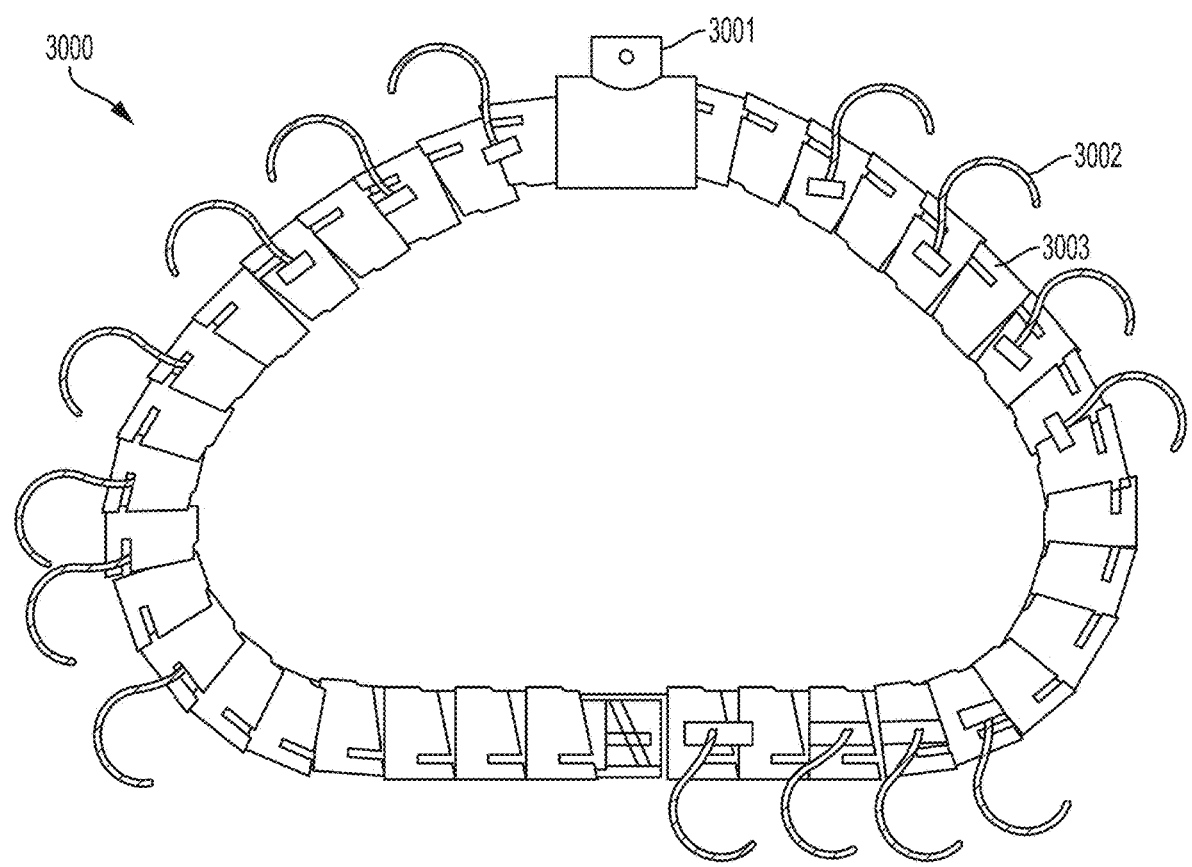
FIG. 30 depicts an illustrative tricuspid ring in a "D" shape geometry.

FIG. 30 shows a perspective view of an embodiment wherein a tricuspid ring 3000 may include one or more snap mechanisms 3001 that connect a proximal and distal end of the laser cut hollow tube to create a geometric shape (e.g., a "D" shape). In a further embodiment, the geometrically shaped tricuspid ring may include one or more anchors 3002 which can be deployed from the deployment windows 3003.

Figure 31:
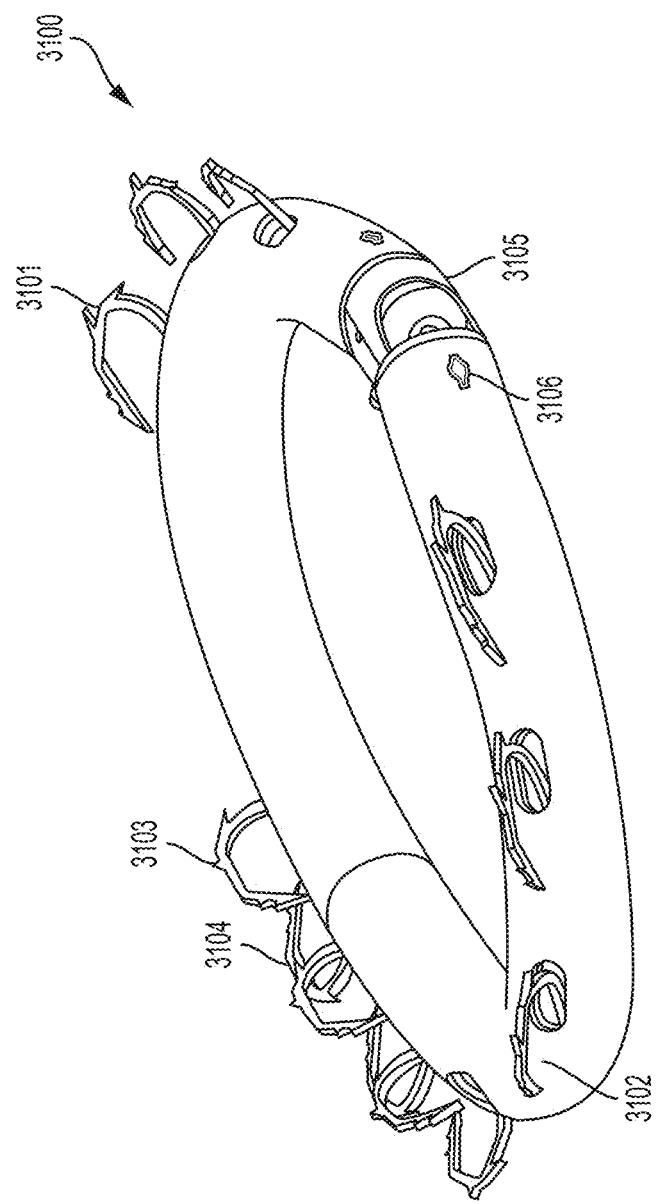
FIG. 31 depicts another illustrative tricuspid ring with a snap mechanism.

FIG. 31 shows a perspective view of an embodiment wherein a tricuspid ring 3100 includes a snap mechanism 3105 that connects a proximal and a distal end of the laser cut hollow tube (700 of FIG. 7) to create a shape that mimics the native shape of the tricuspid annulus. In a further embodiment, the tricuspid ring 3100 may also include one or more anchors deployed from the one or more deployment windows. In one embodiment, as shown in FIG. 31, the anchors may exit from the deployment windows at an angle within a range of about 30 degrees to the horizontal plane to about 75 degrees to the horizontal plane.

Thus, as shown in FIG. 31, an embodiment may include a tricuspid ring 3100, an anterior zone 3101 where the anchors exit from the tricuspid ring at an angle to provide anchoring forces in both the radial and axial directions, a posterior zone 3102 where the anchors exit from the tricuspid ring at an angle to provide anchoring forces in both the radial and axial directions, a first septal zone 3103 where the anchors exit the ring at an angle to provide anchoring forces in both the radial and axial directions, a second septal zone 3104 where the anchors exit from the ring at an angle to provide anchoring forces in both the radial and axial directions, a snapping mechanism (e.g., closure mechanism) 3105, and a suture pin to provide a rotational pin for the sutures 3106.

Figure 32:
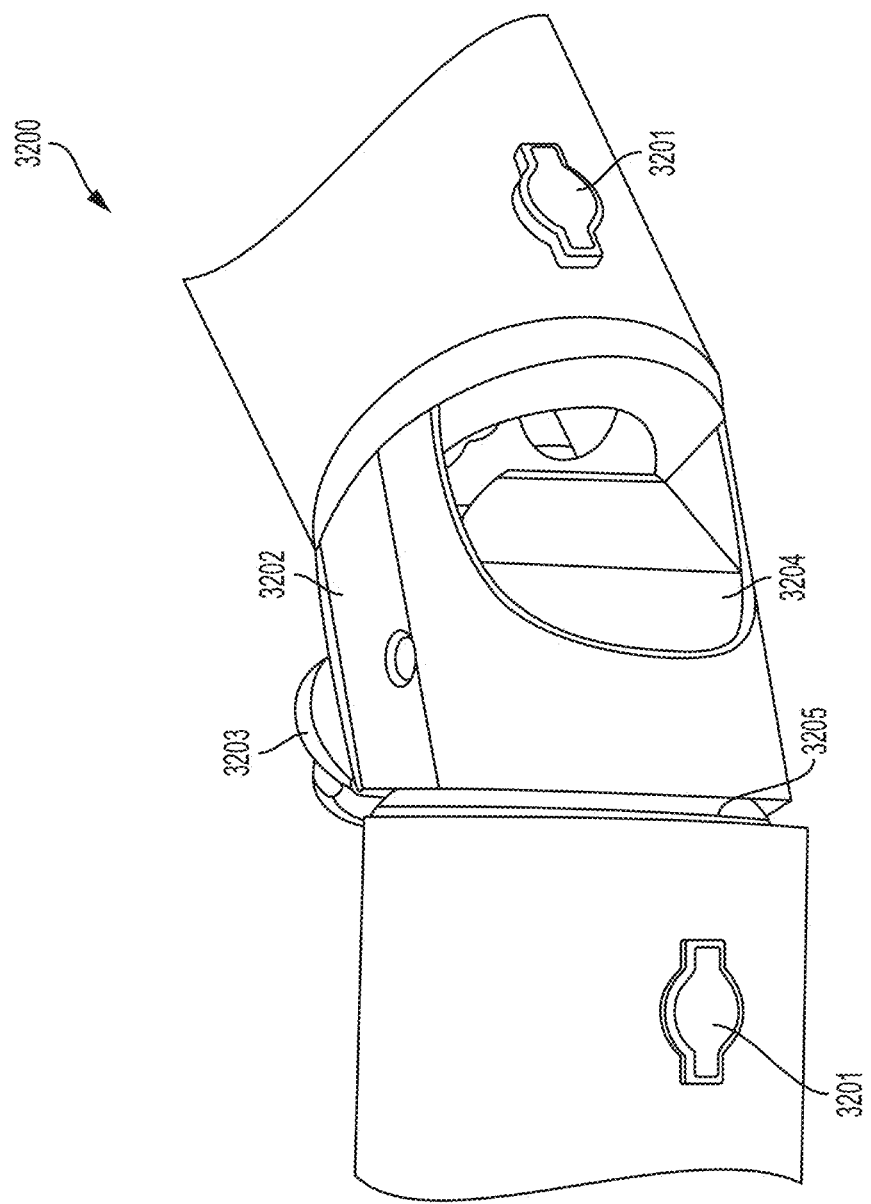
FIG. 32 depicts a detail view of an illustrative snapping mechanism in a closed configuration.

FIG. 32 shows a perspective view of an embodiment wherein a snapping mechanism 3200 is utilized to secure the tricuspid ring in a closed configuration. Thus, as shown in FIG. 32, an embodiment may include a snapping mechanism 3200, a suture pin (e.g., attachment of female and male parts of the ring tube) 3201, a female part of the snapping mechanism 3202, a pivot pin (e.g., attachment of the snapping mechanism to the delivery system with a safety wire) 3203, a cover part (e.g., a component to hold the nitinol disk that snaps the male part into the female) 3204, and a male part of the snapping mechanism 3205.

Figure 33:
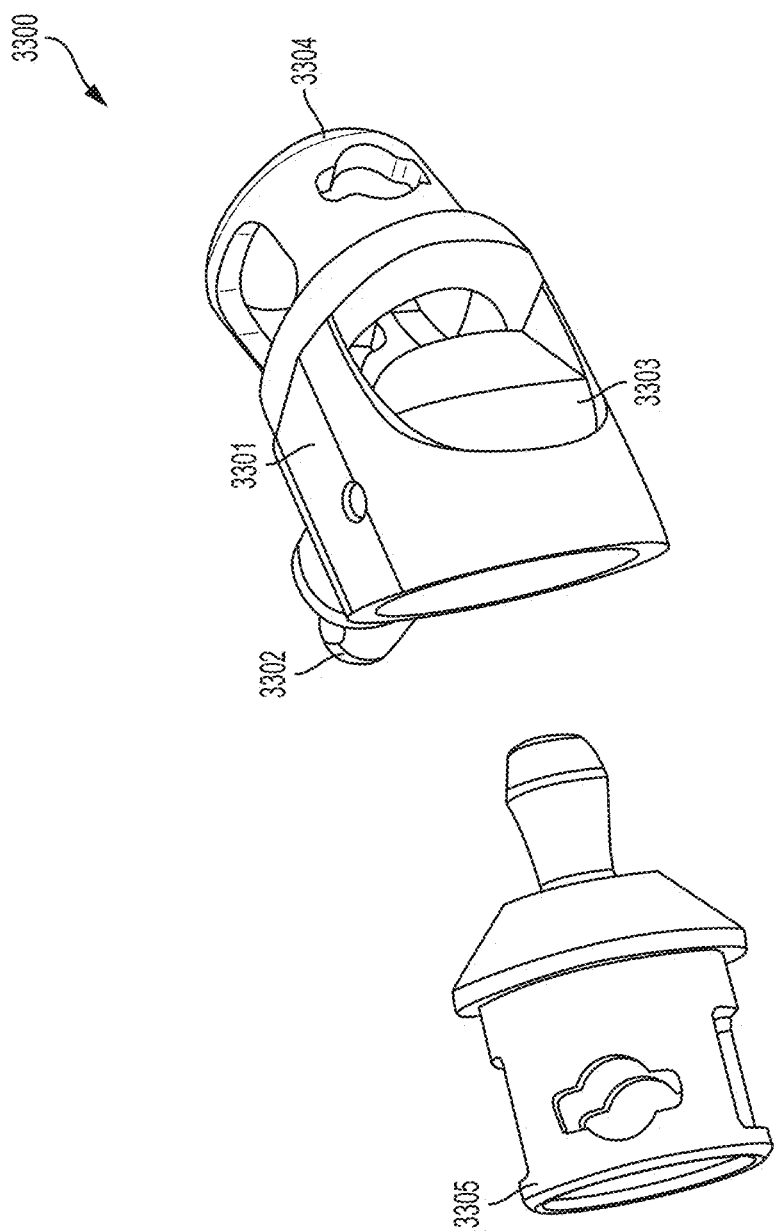
FIG. 33 depicts a detail view of an illustrative snapping mechanism in an open configuration.

FIG. 33 shows a detailed view of an embodiment, wherein the snapping mechanism 3300 is in an open configuration.

Again, similar to embodiments discussed herein, the snapping mechanism 3300 is utilized to secure the tricuspid ring in a closed configuration. Thus, as shown in FIG. 33, an embodiment may include a snapping mechanism 3300, a female part of the snapping mechanism 3301, a pivot pin (e.g., attachment of the snapping mechanism to the delivery system with a safety wire) 3302, a cover part (e.g., a component to hold the Nitinol disk that snaps the male part into the female) 3303, a cup (e.g., an interface of the female to the ring tube) 3304, and a male part of the snapping mechanism 3305.

Figure 34:
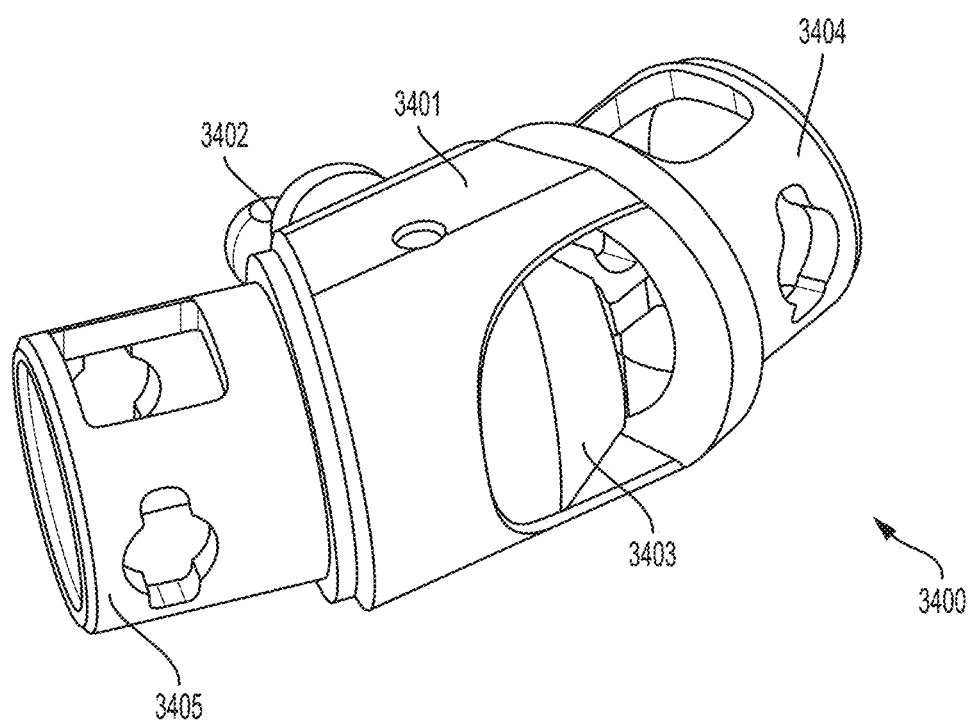
FIG. 34 depicts an isolated detail view of an illustrative snapping mechanism in a closed configuration.

A detailed view of an embodiment where the snapping mechanism is in a closed configuration is shown in FIG. 34. Similar to embodiments discussed herein, the snapping mechanism 3400 is utilized to secure the tricuspid ring in a closed configuration. Thus, as shown in FIG. 34, an embodiment may include a snapping mechanism 3400, a female part of the snapping mechanism 3401, a pivot pin (e.g., attachment of the snapping mechanism to the delivery system with a safety wire) 3402, a cover part (e.g., part to hold the Nitinol disk that snaps the male part into the female) 3403, a cup (e.g., an interface of the female to the ring tube) 3404, and a male part of the snapping mechanism 3405.

Figure 35:
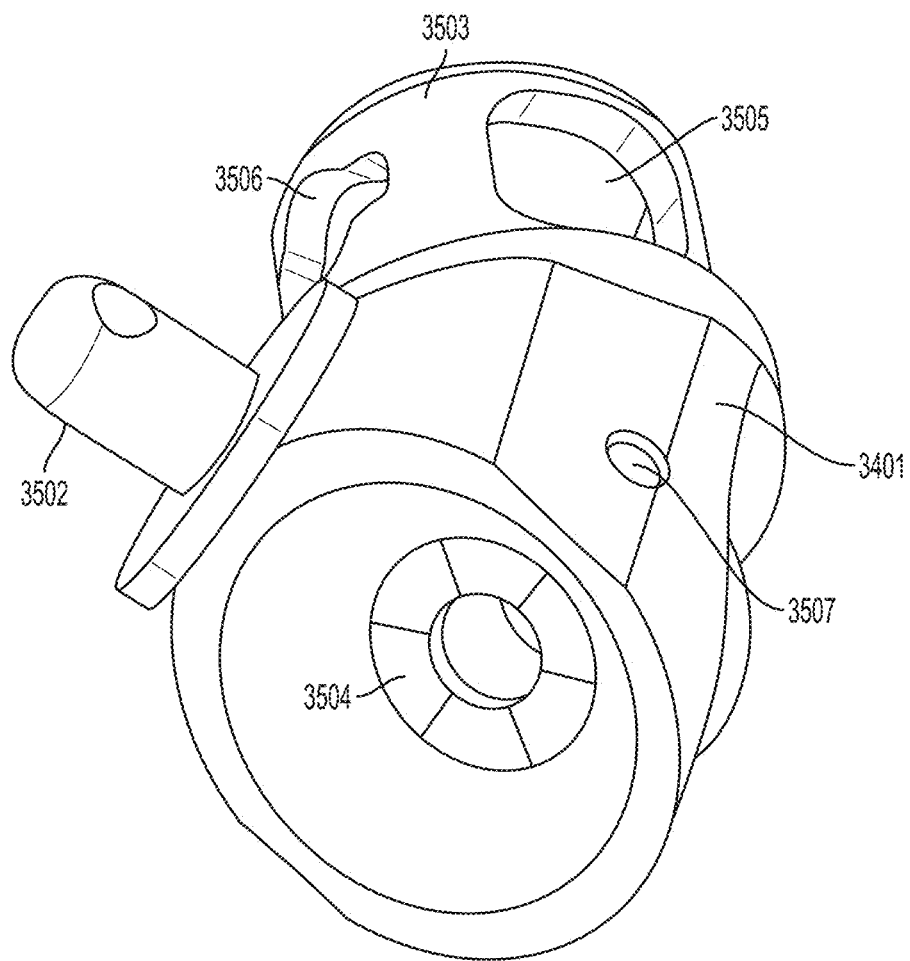
FIG. 35 depicts an isolated detail view of an illustrative female snapping mechanism.

A detailed view of the female part 3401 of the snapping mechanism 3400 according to one embodiment is shown in FIG. 35. As shown in FIG. 35, the female part 3401 of the snapping mechanism 3400 may include, a pivot pin (e.g., an attachment of the snapping mechanism to the delivery system with a safety wire) 3502, a cup (e.g., an interface of the female to the ring tube) 3503, a nitinol disk for locking the snap into position 3504, a window for suture routing 3505, a window for a suture pin 3506, and a gold marker 3507.

Figure 36:
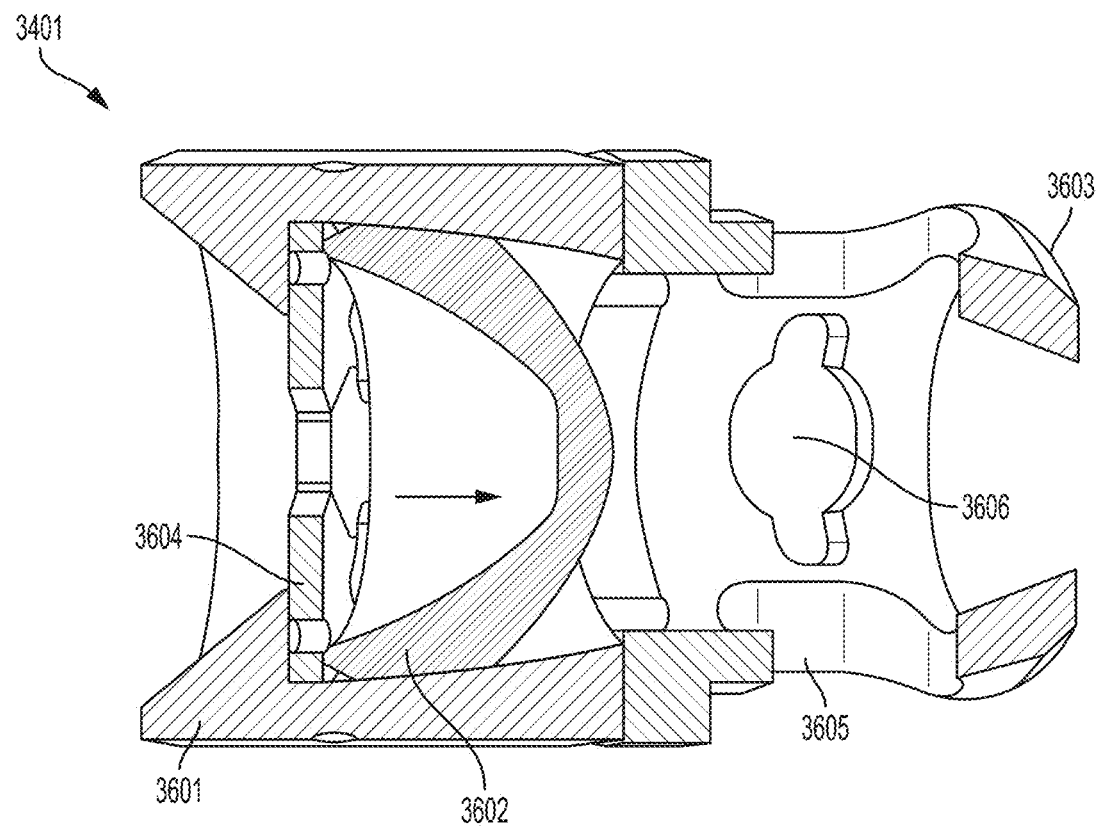
FIG. 36 depicts a cross-sectional view of an illustrative female snapping mechanism.

FIG. 36 shows an illustrative cross section of the female part 3401 of the snapping mechanism 3400 according to an embodiment. As shown in FIG. 36, the female part 3401 of the snapping mechanism 3400 may include a pivot pin (e.g., an attachment of the snapping mechanism to the delivery system with a safety wire) (not shown), a cover that holds a nickel titanium (Ni—Ti) disk 3602, a cup (e.g., an interface of the female to the ring tube) 3603, a nitinol disk for locking the snap into position (tongues can open only in one direction to prevent un-intentional unsnapping) 3604, a window for suture routing 3605, and a window for a suture pin 3606.

Figure 37:
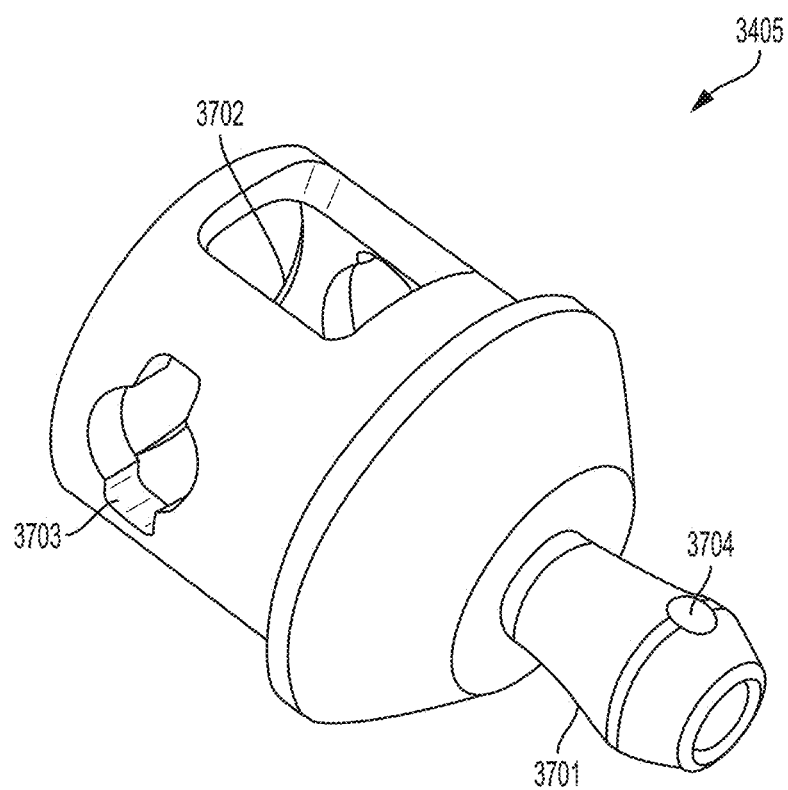
FIG. 37 depicts a detail view of an illustrative male snapping mechanism.

A detailed view of the male part 3405 of the snapping mechanism according to an embodiment is shown in FIG. 37. As shown in FIG. 37, the male part 3405 of the snapping mechanism 3400 may include a male cone 3701 to allow smooth entrance and locking of the male within the female, a least one window for suture routing 3702, at least one window for a suture pin 3703, and at least one protrusion 3704 upon the suture pin.

Figure 38:
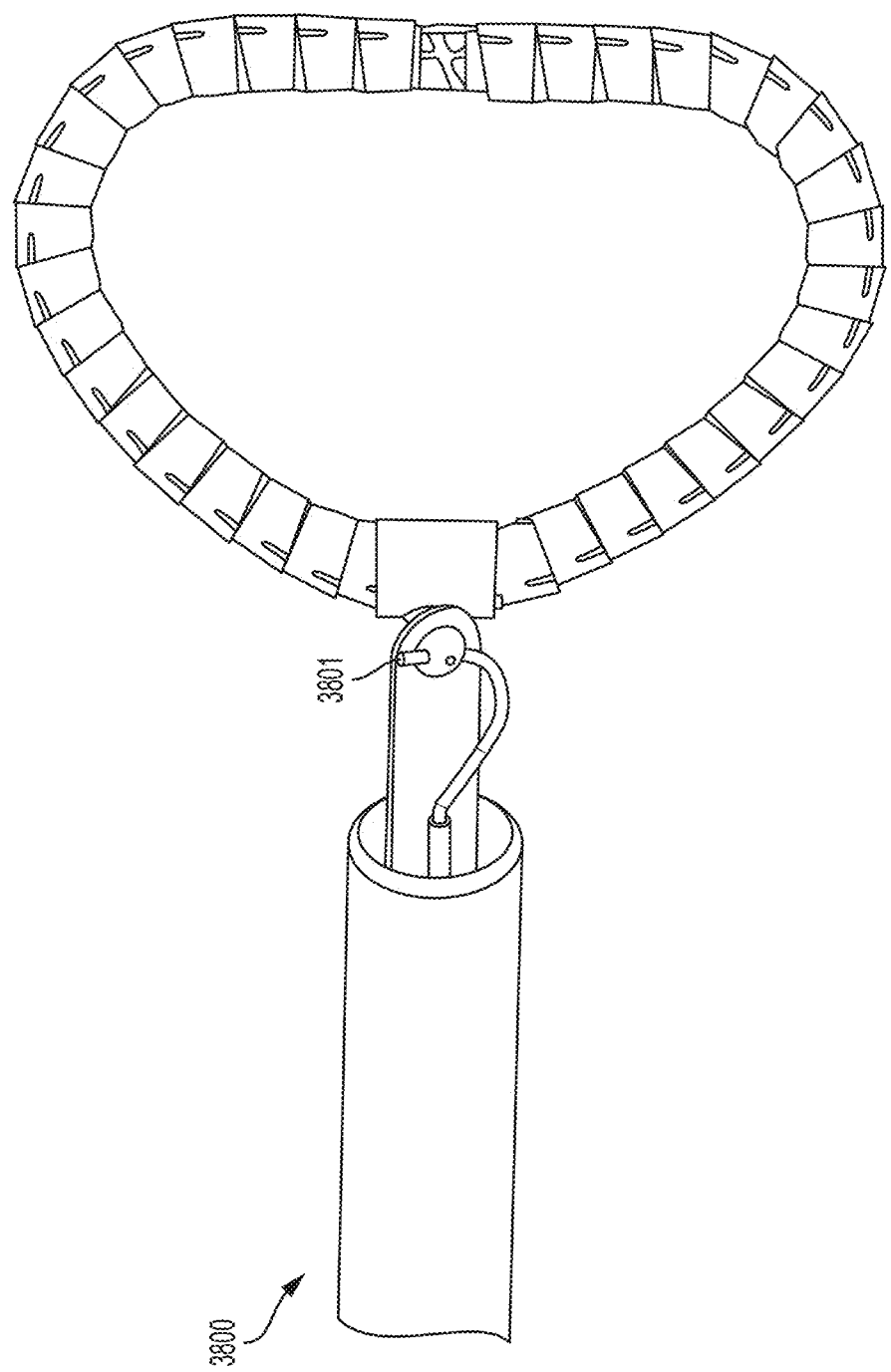
FIG. 38 depicts a view of an illustrative delivery system that is connected to a snapped ring.

Turning now to FIG. 38, a detailed view of a distal end of a delivery system is shown. In one embodiment, the distal end of the delivery system may interface with the tricuspid ring assembly. For example, FIG. 39 illustrates a detailed view of the distal end 3901 of the delivery system 3900, wherein the delivery system interfaces with the tricuspid ring assembly and the tricuspid ring 3950.

Figure 39:
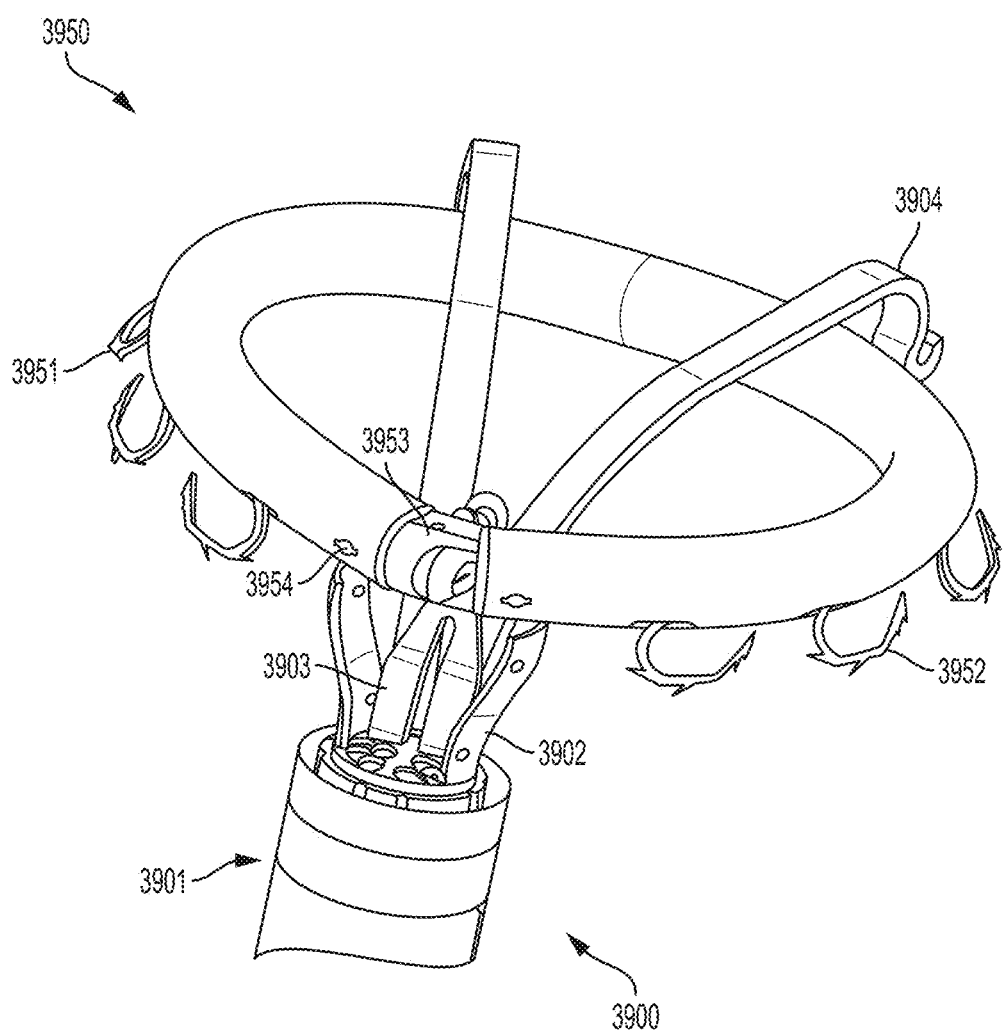
FIG. 39 depicts another view of an illustrative delivery system that is connected to a ring with deployed anchors with the stabilizing tool in the center.

As shown in FIG. 39, the delivery system 3900 may interface with a tricuspid ring 3950 that may have an anterior zone 3951 where anchors exit the ring at an angle to provide anchoring forces in both the radial and axial direction. The tricuspid ring 3950 may also have a posterior zone 3952 where anchors exit the tricuspid ring at an angle to provide anchoring forces in both the radial and axial direction, a snapping mechanism (e.g., closure mechanism) 3953, and a suture pin to provide a rotation pin for the sutures 3954. The delivery system 3900 may include a distal end of the guiding catheter 3901, a stabilizing mechanism to ensure ring stabilization during an implantation procedure 3902, a delivery system (DS) tongue (e.g., ring interface device) 3903, and a stabilizing tool 3904.

Figure 40:
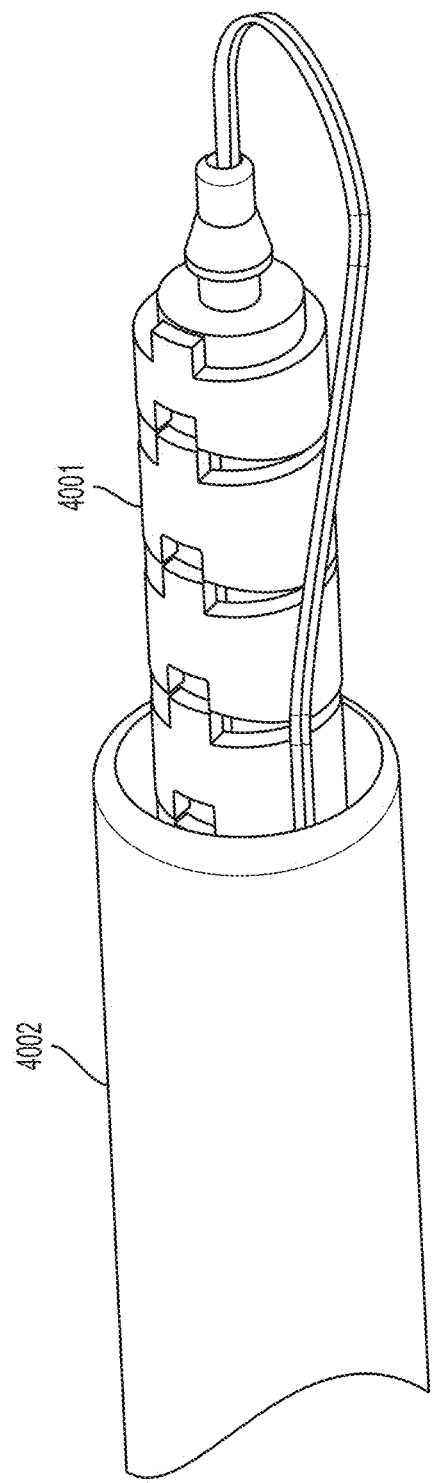
FIG. 40 depicts an illustrative view of the delivery system.
Figure 41:
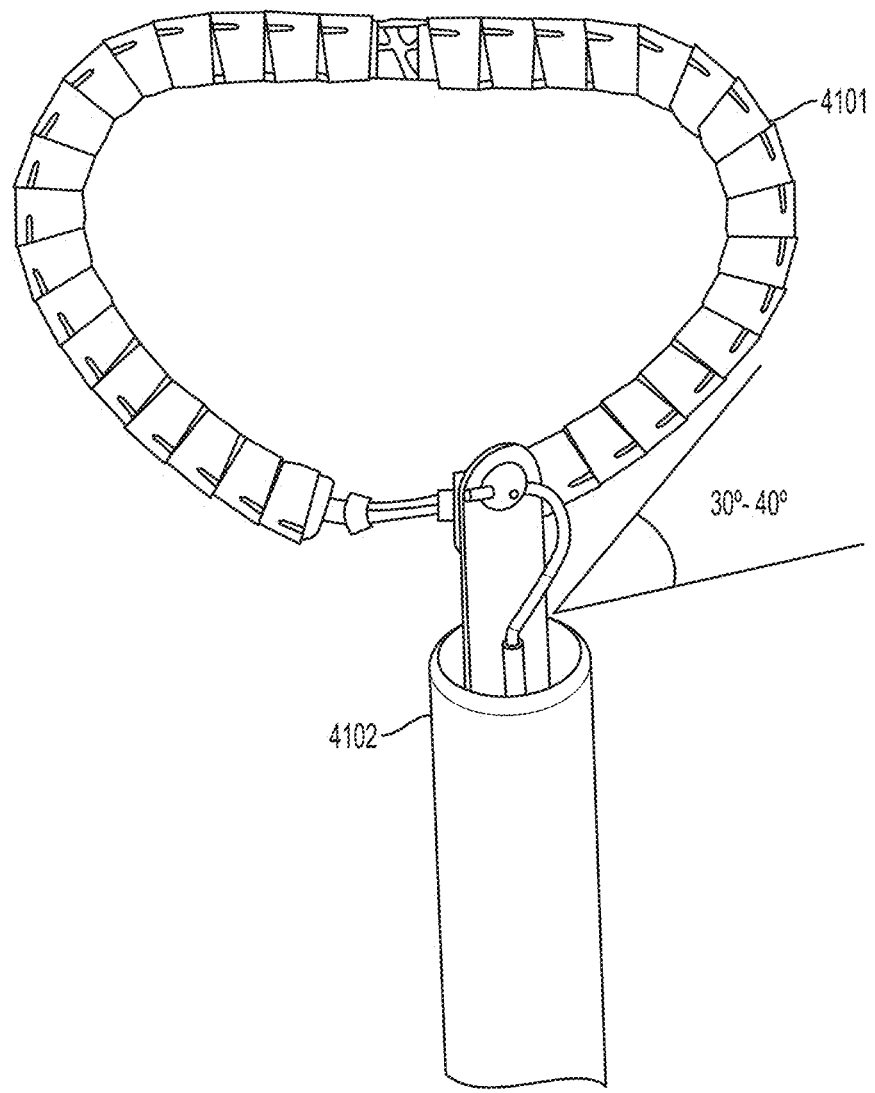
FIG. 41 depicts another illustrative view of the delivery system connected to a deployed ring.
Figure 42:
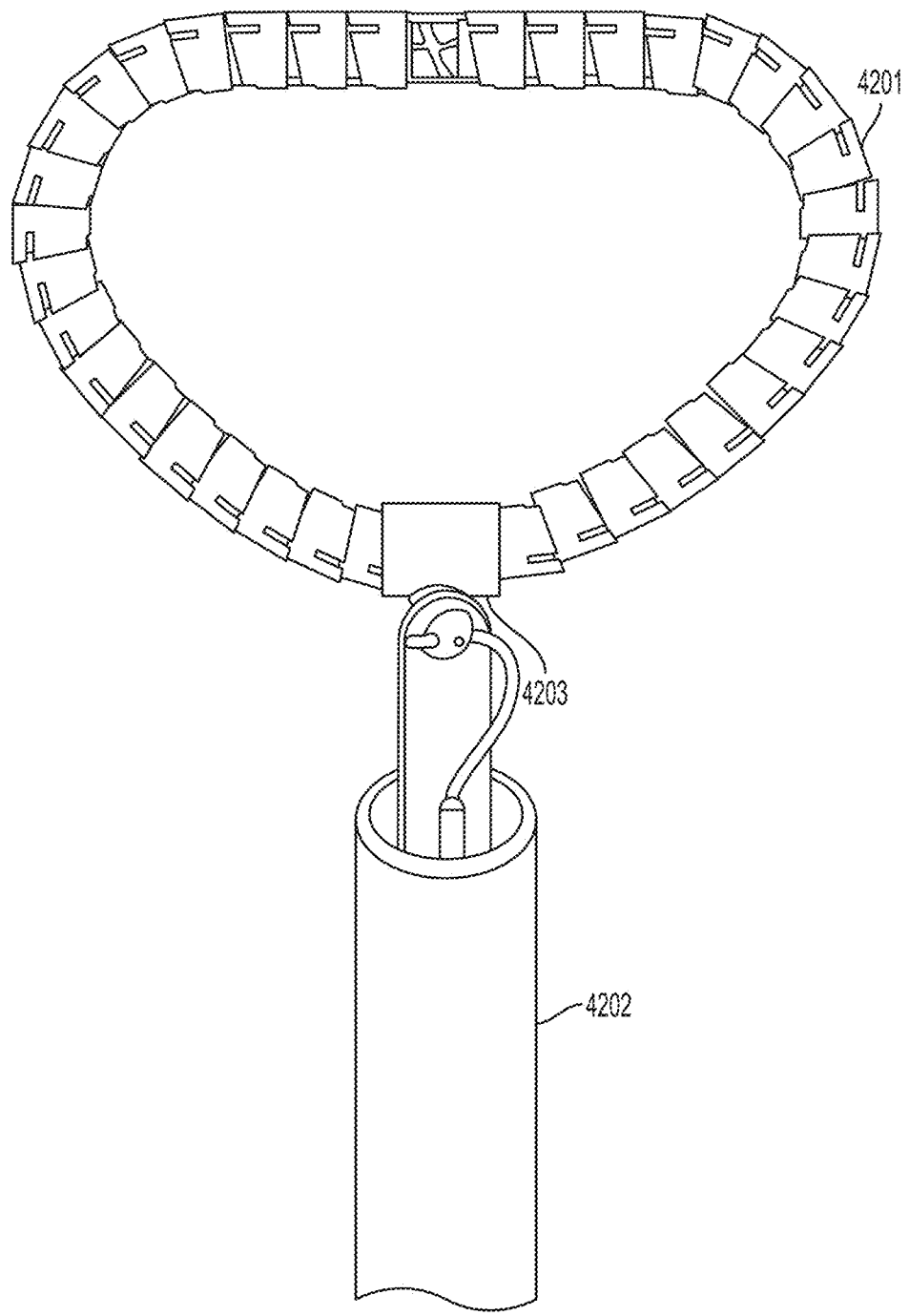
FIG. 42 depicts another illustrative view of the delivery system that is connected to a ring.

FIGS. 40-42 depict various views of the delivery system during the beginning of the deployment of the tricuspid ring from the delivery system. In one embodiment, and as shown in FIG. 40, the tricuspid ring 4001 may exit the delivery system 4002 in a linear shape. Once the tricuspid ring 4001 exits the delivery system, it may in some embodiments be formed into a ring-like shape using methods disclosed herein, and as shown in FIGS. 41 and 42. FIG. 41 shows an embodiment in which the tricuspid ring 4101 is formed using the delivery system 4102. In some embodiments, and as shown in FIG. 41, the tricuspid ring 4101 may be between about 30° and about 40° from a plane normal to the delivery system 4102. FIG. 42 shows an embodiment in which the tricuspid ring 4201 is formed and the snapping mechanism (e.g., closure mechanism) 4203 secures the ring in the proper geometry. In some embodiments, such as that shown in FIG. 42, the delivery system 4202 may be used to move or modify the shape or location of the tricuspid ring 4201.

Figure 43:
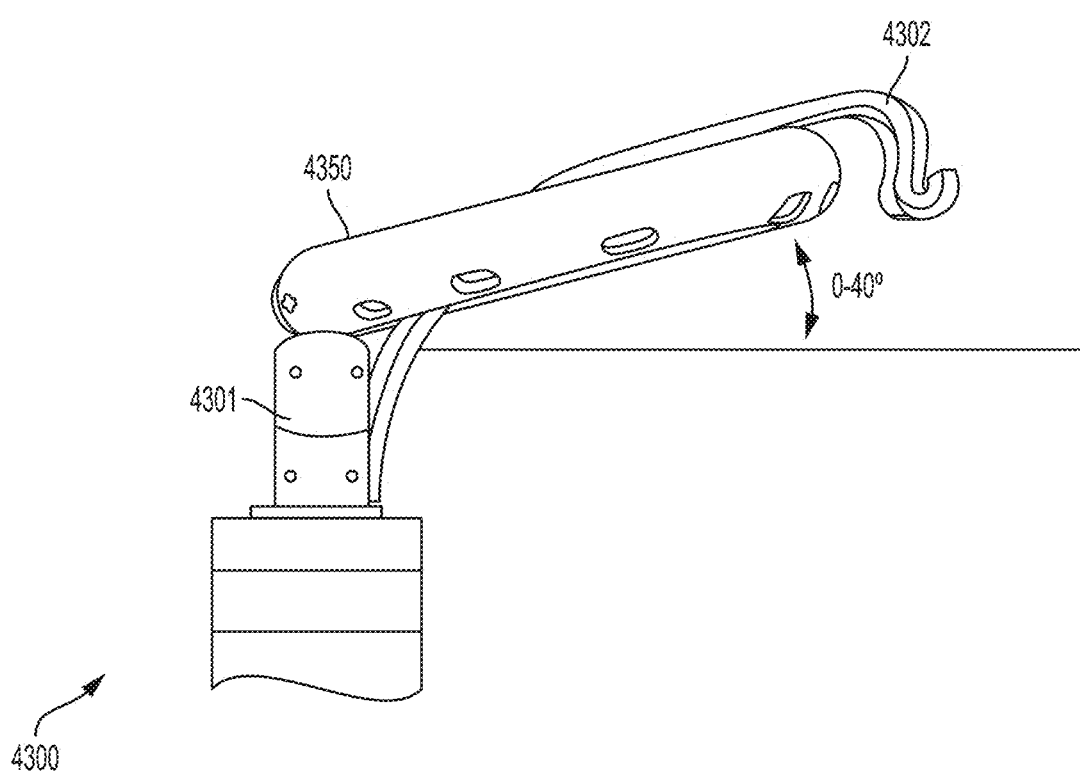
FIG. 43 depicts another illustrative view of a hinge system associated with the delivery system and a stabilizing tool.

In some embodiments, such as that shown in FIG. 43, the delivery system 4300 may interface with a tricuspid ring 4350. The tricuspid ring 4350 may also have a posterior zone where anchors exit the tricuspid ring (not shown) at an angle to provide anchoring forces in both the radial and axial direction, a snapping mechanism (e.g., closure mechanism) (not shown), and a suture pin to provide rotation pin for the sutures (not shown). The delivery system 4300 may include a distal end of the guiding catheter (not shown), a stabilizing mechanism 4301 to ensure ring stabilization during an implantation procedure, a delivery system (DS) tongue (e.g., ring interface device) (not shown), and a stabilizing tool 4302. As shown, the plane of the tricuspid ring 4350 may be between about 0° and about 40° removed from the plane of the tricuspid valve after rotation around the hinge.

Figure 44:
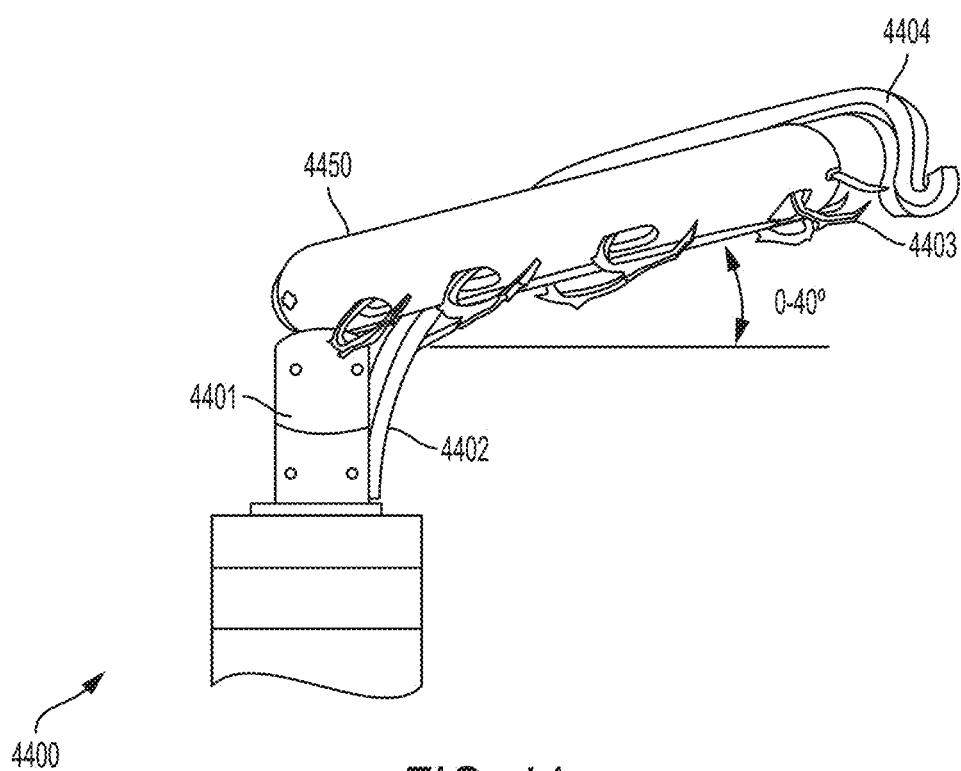
FIG. 44 depicts an illustrative view of a delivery system connected to a fully deployed ring and stabilizing tool.

In another embodiment, as shown in FIG. 44, the plane of the ring may be parallel or slightly angled (e.g., from about 0° to about 40°) to the plane of the tricuspid valve after rotation around the hinge. Thus, an embodiment may utilize a trans-apical approach (i.e., pulling the ring to the tissue). In some embodiments, the delivery system 4400 may interface with a tricuspid ring 4450 that may have an anterior zone where anchors (not shown) exit the ring at an angle to provide anchoring forces in both the radial and axial direction. The tricuspid ring 4450 may also have a posterior zone 4403 where anchors exit the tricuspid ring at an angle to provide anchoring forces in both the radial and axial direction, a snapping mechanism (e.g., closure mechanism) (not shown), and a suture pin to provide a rotation pin for the sutures (not shown). The delivery system 4400 may include a distal end of the guiding catheter 4401, a stabilizing mechanism 4402 to ensure ring stabilization during an implantation procedure, a delivery system (DS) tongue (e.g., ring interface device) (not shown), and a stabilizing tool 4404. As stated, the ring orientation in relation to the delivery system 4400 may be in a range of about 0 degrees to about 40 degrees "above" the horizontal plane. As discussed herein, this approach is trans-apical, thus pulling the ring to the tissue. In a further embodiment, the ring orientation may be in a range of about 0 degrees to about 40 degrees "above" the horizontal plane of the delivery system. FIG. 44 depicts the embodiment of FIG. 43 with the anchors deployed.

Figure 45:
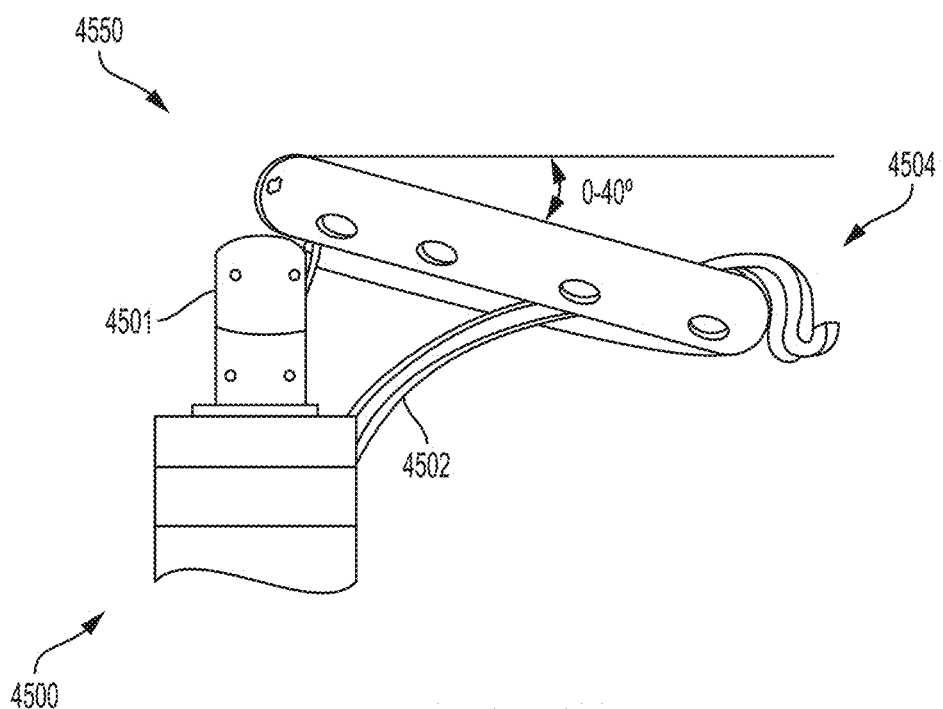
FIG. 45 depicts another illustrative view of a hinge system associated with the delivery system.
Figure 46:
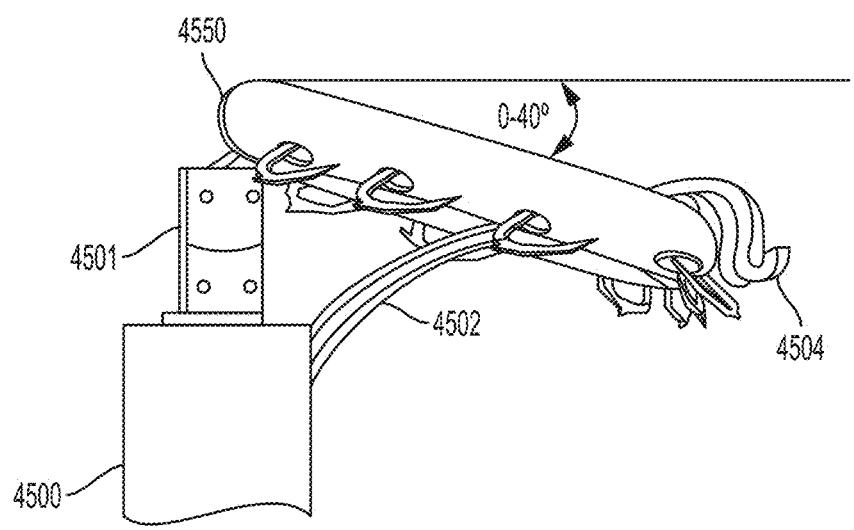
FIG. 46 depicts another illustrative view of a delivery system that is connected to a deployed ring while being manipulated by a stabilizing tool and before anchors are deployed.

In another embodiment, as shown in FIG. 45, the position of the tricuspid ring may be parallel to or below the plane of the tricuspid valve after rotation around the hinge. Again this approach is trans-apical, thus pulling the ring to the tissue. However, FIG. 45 differs from the embodiment of FIGS. 43-44, in that the ring orientation in relation to the delivery system may be in a range of about 0 degrees to about 40 degrees "below" the horizontal plane. In an additional embodiment, as shown in FIG. 45, the position of the tricuspid ring after rotation around the hinge may be parallel or slightly below to the plane of the tricuspid valve. The ring orientation, in this embodiment, in relation to the delivery system may be in a range of about 0 degrees to about 40 degrees "below" the horizontal plane. FIG. 46 depicts an embodiment with the anchors deployed.

As shown in FIGS. 45-46, in some embodiments, the delivery system 4500/4600 may interface with a tricuspid ring 4550 that may have an anterior zone where anchors (not shown) exit the ring at an angle to provide anchoring forces in both the radial and axial direction. The tricuspid ring 4550 may also have a posterior zone where anchors exit the tricuspid ring at an angle to provide anchoring forces in both the radial and axial direction, a snapping mechanism (e.g., closure mechanism) (not shown), and a suture pin to provide a rotation pin for the sutures (not shown). The delivery system 4500 may include a distal end of the guiding catheter 4501, a stabilizing mechanism to ensure ring stabilization during an implantation procedure 4502, a delivery system (DS) tongue (e.g., ring interface device) (not shown), and a stabilizing tool 4504.

Figure 47:
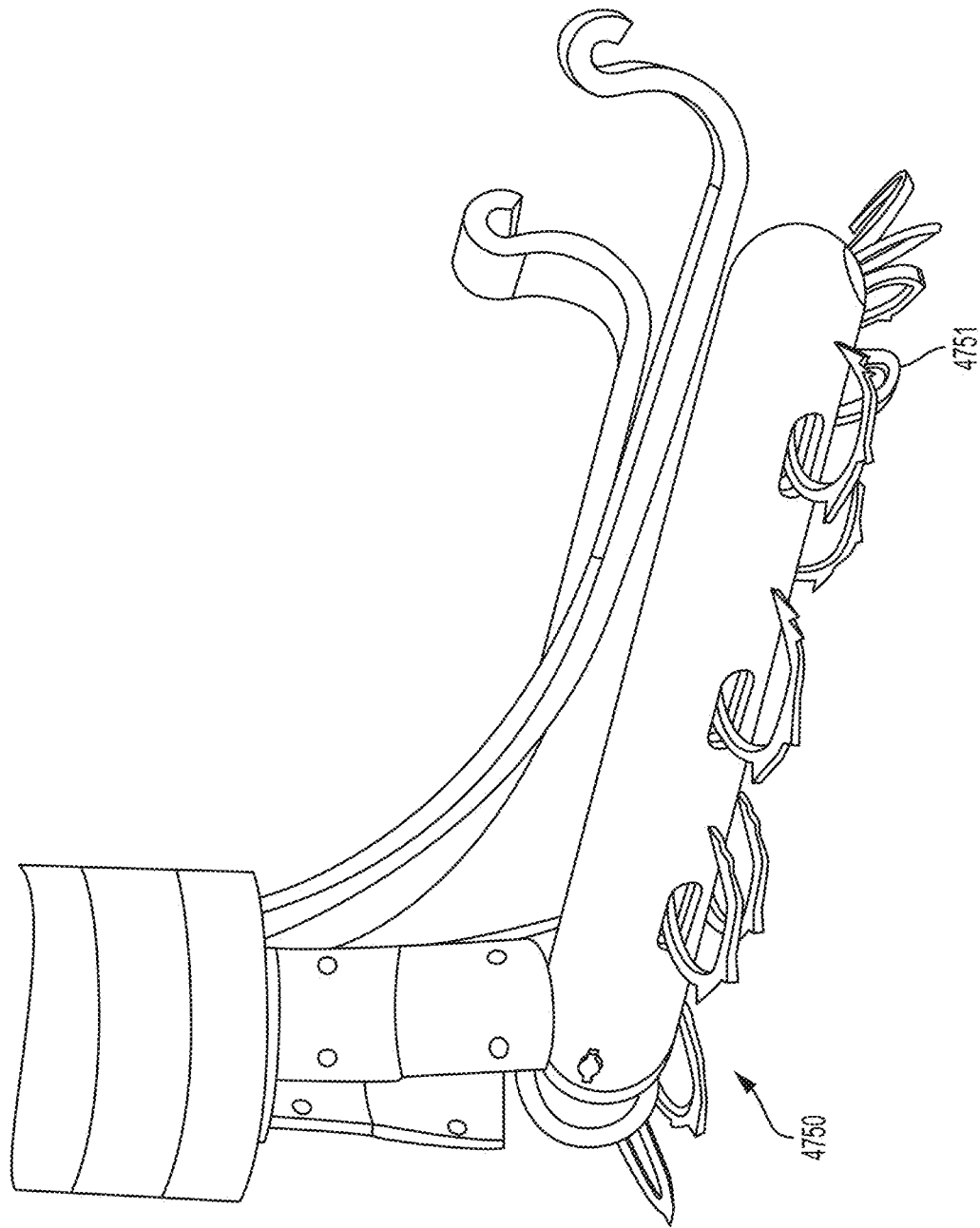
FIG. 47 depicts another illustrative view of a hinge system associated with the delivery system.

FIG. 47 shows a zoomed in view of the tricuspid ring 4750 after rotation around the hinge whereby the plane of the ring may be parallel to the plane of the tricuspid valve. The approach may be trans-atrial, trans-septal, and/or trans-jugular, thus pulling the ring to the tissue. In an embodiment, as shown in FIG. 47, the ring orientation in relation to the delivery system may be in a range of about 0 degrees to about 40 degrees "below" the horizontal plane, and the anchors may or may not be deployed.

Figure 48:
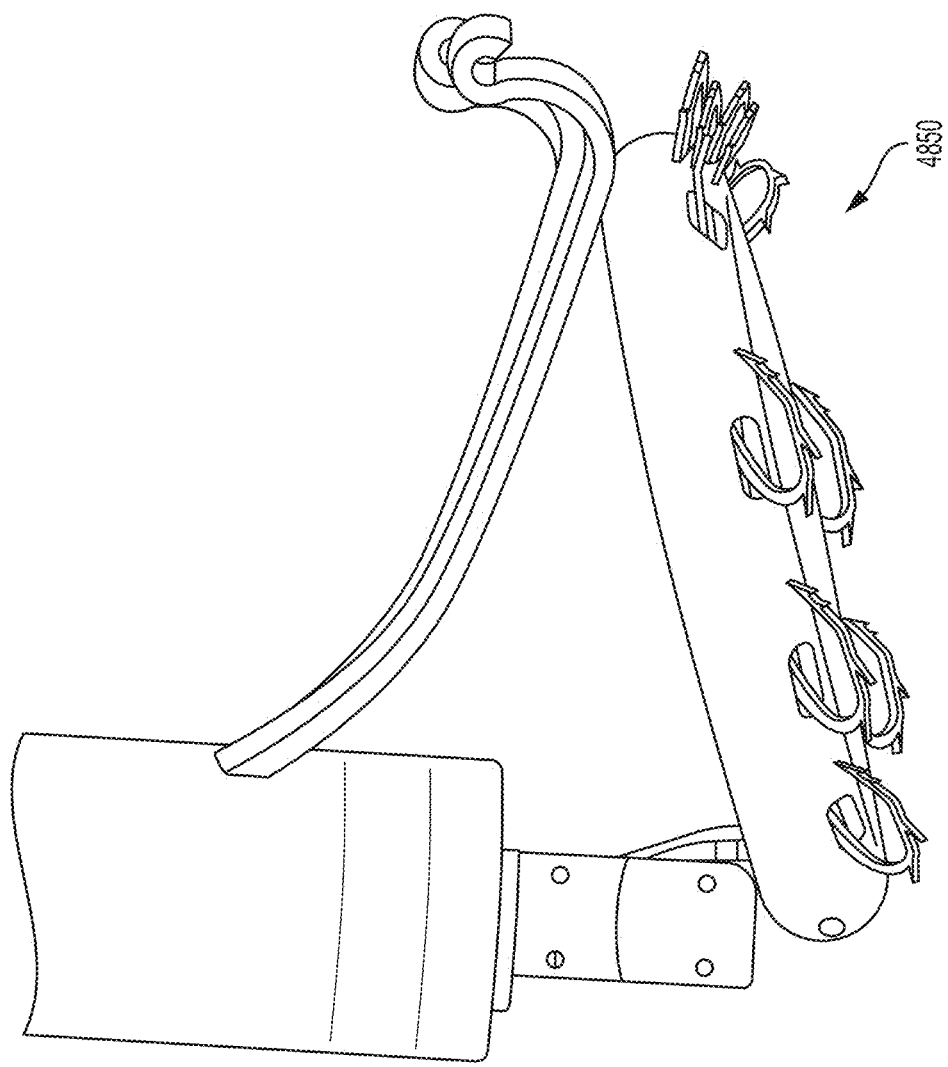
FIG. 48 depicts another illustrative view of a hinge system associated with the delivery system.

Additionally or alternatively, FIG. 48 shows a zoomed in view of the tricuspid ring 4850 after rotation around the hinge whereby the plane of the ring is parallel to the plane of the tricuspid valve. The approach of FIG. 48 may also be trans-atrial, trans-septal, and/or trans-jugular, thus pulling the ring to the tissue. In another embodiment, as shown in FIG. 48, the ring orientation in relation to the delivery system may be in a range of about 0 degrees to about 40 degrees "above" the horizontal plane, and the anchors 4751 may or may not be deployed.

Figure 49:
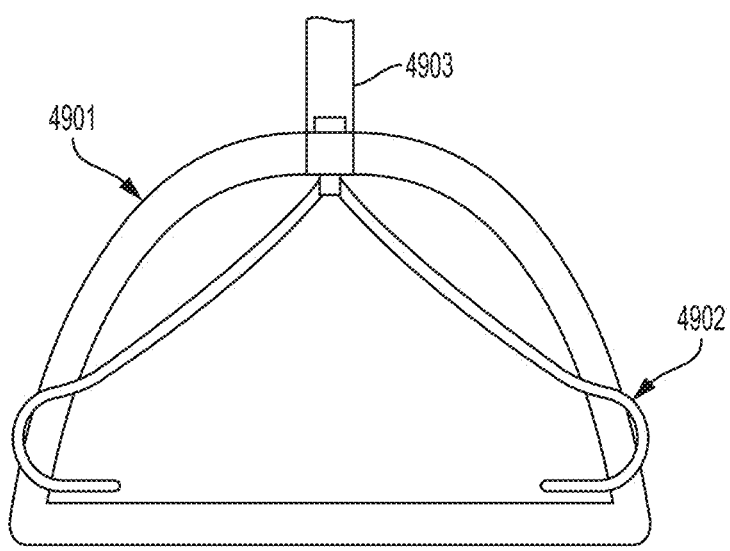
FIG. 49 depicts an illustrative view of a stabilizing tool and tricuspid ring.
Figure 50:
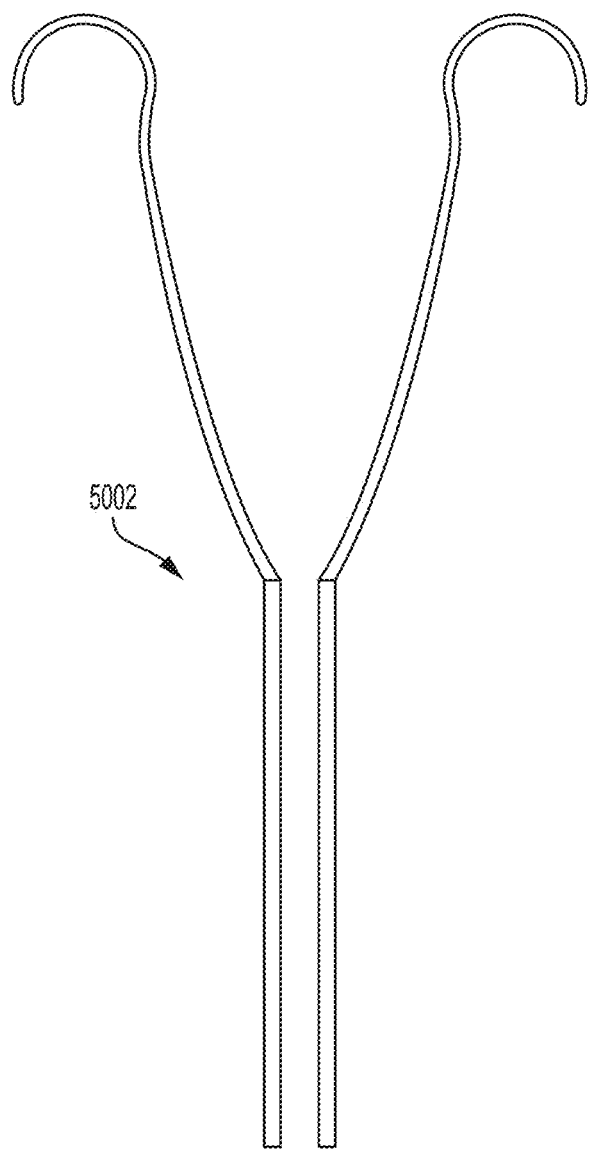
FIG. 50 depicts an isolated illustrative view of a stabilizing tool.

Referring now to FIGS. 49-50, an embodiment shows the geometry of the stabilizing tool that may be needed for the placement of the tricuspid ring 4901 above the annulus. By way of non-limiting example, FIG. 49 shows the tricuspid ring 4901, which may comprise various zones, and its interaction with the stabilizing tool 4902. In one embodiment, the stabilizing tool 4902 may be incorporated or attached to the delivery system 4903, as shown in FIG. 49. A more detailed view of the stabilizing tool is shown in FIG. 50. In some embodiments, the stabilizing tool 5001 may be made of super elastic nickel titanium (Ni—Ti) from a laser cut hypotube.

Figure 51:
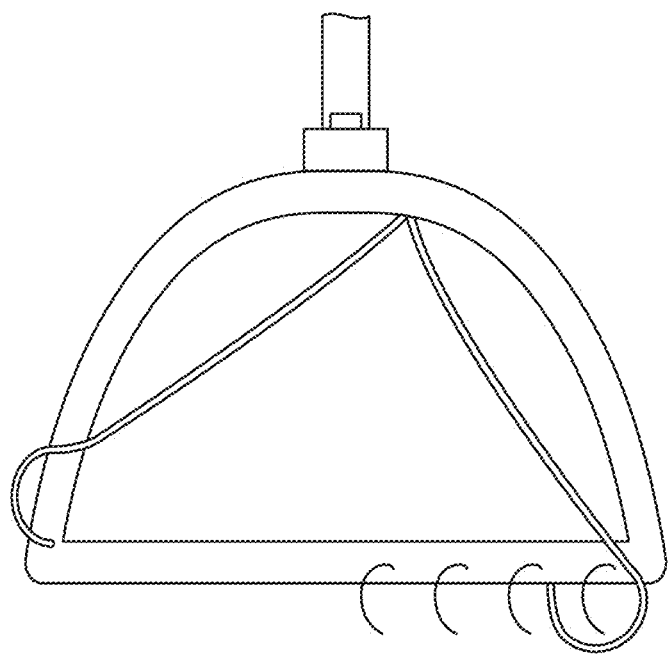
FIG. 51 depicts an illustrative view of deployed anchors at the septal zone.
Figure 52:
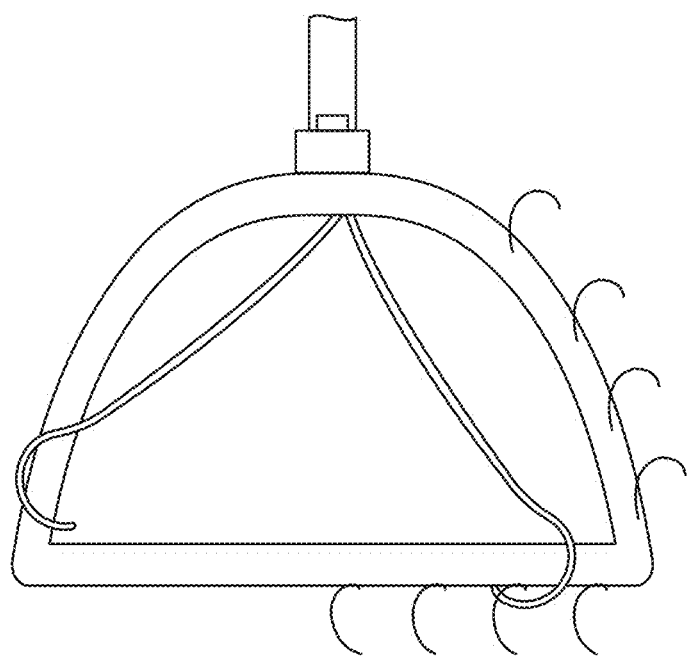
FIG. 52 depicts another illustrative view of deployed anchors at the septal and posterior zones.
Figure 53:
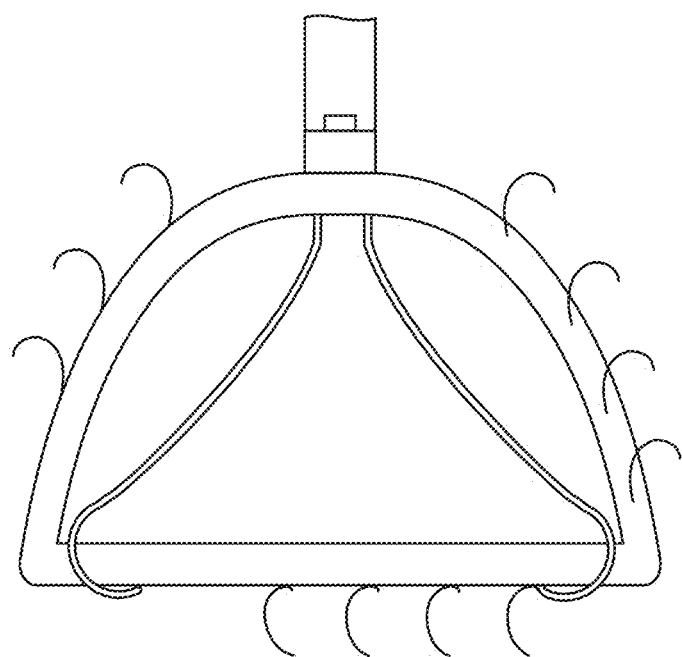
FIG. 53 depicts another illustrative view of deployed anchors at the septal zone, posterior zone, and first anterior zone.
Figure 54:
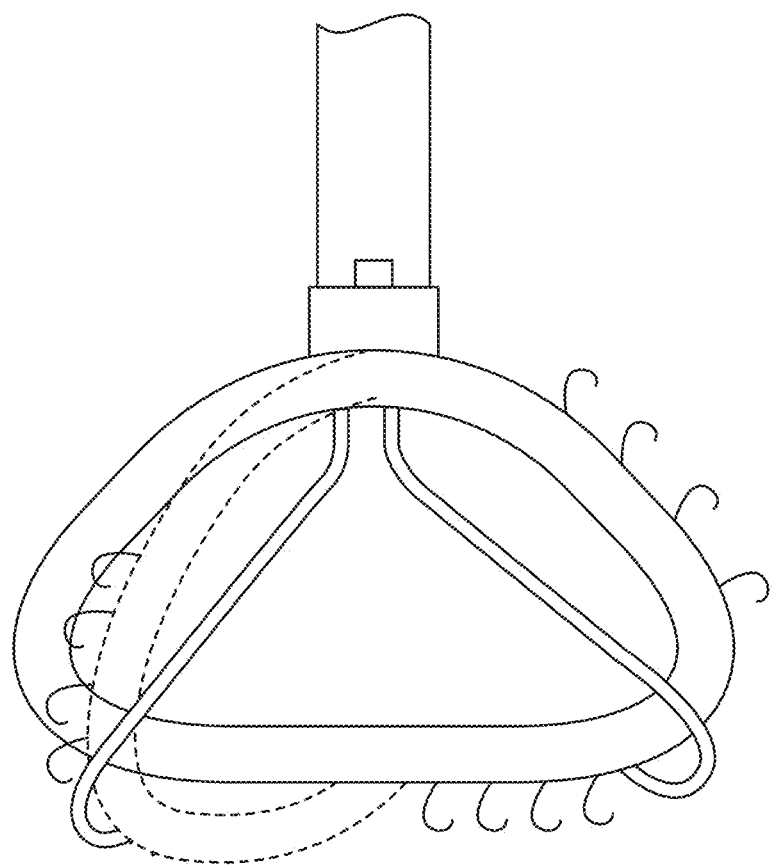
FIG. 54 depicts another illustrative view of a stabilizing tool and tricuspid ring with deployed anchors at all zones.

FIGS. 51-54 depict an illustrative ring as it is placed in the annulus, and the deployment of the anchors into the tricuspid annulus. In particular, FIG. 51 depicts the deployment of the septal anchors into the septal section of the tricuspid annulus adjacent to the septal leaflet. Additionally, FIG. 52 shows the deployment of the posterior anchors into the posterior section of the annulus adjacent to the posterior leaflet. FIG. 53 shows the additional deployment of the first zone of the anterior anchors that are adjacent to the anterior leaflet. FIG. 54 shows dragging of the anterior leaflet (e.g., by the stabilizing tool) as a means to reduce the dilation of the annulus and as a consequence, improve the coaptation of the anterior leaflet and the septal leaflet.

Figure 55:
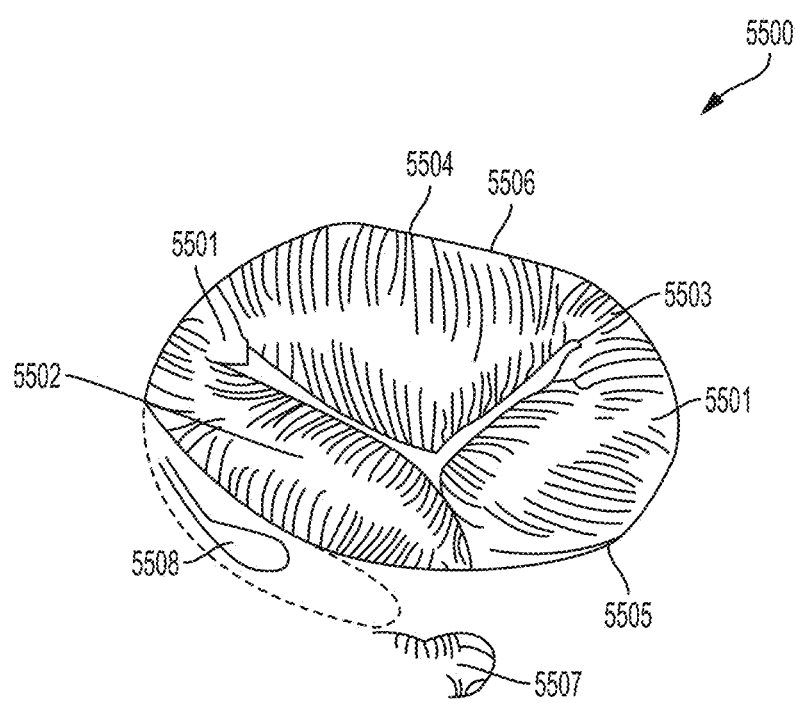
FIG. 55 depicts an illustrative view of a tricuspid valve.
Figure 56:
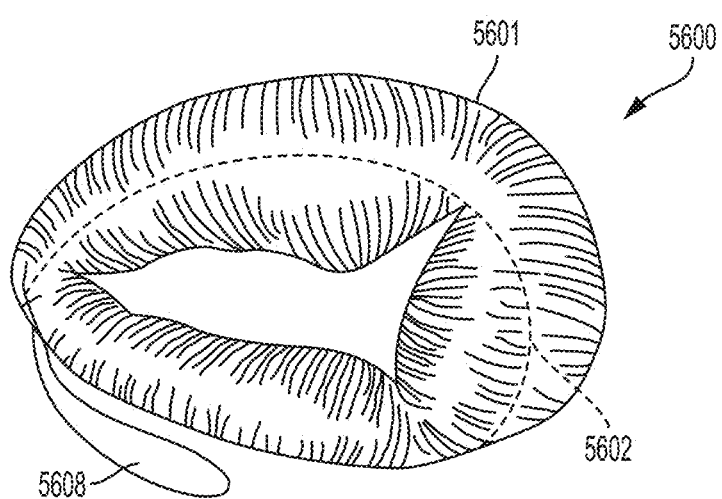
FIG. 56 depicts another illustrative view of a tricuspid valve.

FIGS. 55-56 shows further illustrative embodiments of a tricuspid valve 5500/5600. With reference to FIG. 55, it should be understood that a tricuspid valve 5500 may include: an anteroseptal commissure 5501, a septal leaflet 5502, an anteroposterior commissure 5503, an anterior leaflet 5504, a posteroseptal commissure 5505, an annulus 5506, a coronary sinus 5507, and an AV node 5508. As shown in FIG. 56, the annulus of tricuspid valve 5600 may be dilated. A dilated annulus shape 5601 is shown alongside a normal sized annulus (i.e., the desired shape if a tricuspid ring) 5602 (dashed lines) as a non-limiting example for clarity purposes. The tricuspid valve 5600 may also include an AV node 5608.

Accordingly, systems and methods are provided for introducing a tricuspid ring (e.g. while it is housed in a linear shape within the delivery system) in a trans-apical or trans-femoral approach. In an embodiment, the distal tip of the delivery system may be introduced above the tricuspid annulus. Once the tricuspid ring is introduced, the plane of the tricuspid ring may be rotated (e.g., automatically) to be parallel to the plane of the tricuspid annulus.

The tricuspid ring may then be snapped into a proper shape (e.g., a "D" shape) and introduced to the stabilization tool. The shape is possible because, as discussed herein, the tricuspid ring comprises an outer hollow member with a plurality of segments, wherein the segments may be adjustable and may cooperate with one another in order to change the outer hollow member from an annular operable shaped geometry to an elongated insertion shaped geometry and vice versa.

Once the tricuspid ring is properly controlled by the stabilization tool (e.g., as depicted in FIGS. 38-54), the properly shaped (e.g., "D" shaped) tricuspid ring may be inserted and guided to the desired location within the patient (e.g., the tricuspid valve). Once in the proper location, an embodiment may deploy a plurality of anchors. For example, an embodiment may deploy anchors associated with the septal zone, the posterior zone, or the first or second anterior zones.

In a further embodiment, the anchored tricuspid ring is anchored towards the septal leaflet, thereby reducing the height of the anterior-septal leaflets by approximately 15% to 20%. One or more second anterior zone anchors may also be deployed. In another embodiment, the design of the tricuspid ring may not include anchors in certain zones (e.g., the AV node zone). As discussed herein, this may be due to a particular zone being sensitive to external forces which could lead to adverse effects for the patient such as Arrhythmia, an irregular heart rhythm or heart failure.

Additionally or alternatively, the tricuspid ring (e.g., the septal zone and the posterior zone) may be dragged by the stabilizing tool to reduce the height of the anterior-septal leaflet height prior to the anchors in the first and second anterior zones one and two being applied.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A device for minimally invasive medical treatment comprising:
    a hollow tube comprising:
        a first end;
        a second end;
        an exterior having a plurality of cutouts;
        at least one snap mechanism configured to connect the first end and the second end together;

a plurality of anchor deployment zones;

a plurality of anchors configured to deploy through the plurality of cut outs, each anchor of the plurality of anchors being associated with at least one of the plurality of anchor deployment zones, wherein each of the plurality of anchor deployment zones are configured to operate independently;

at least one anchor stop mechanism that comprises a projection configured to hold the plurality of anchors in place and prevent premature deployment of the plurality of anchors, wherein the projection projects a predetermined height from an anchor rail, wherein the anchor rail comprises some of the plurality of anchors coupled thereto; and at least one stabilizing mechanism configured to be disengaged from the hollow tube after insertion.

2. The device of claim 1, wherein the plurality of cutouts are laser cutouts.

3. The device of claim 1, wherein the plurality of cutouts comprise windows; and wherein the plurality of anchors exit the exterior of the hollow tube using the windows.

4. The device of claim 1, wherein the hollow tube is configured to take a geometric D shape when the first end and second end are connected.

5. The device of claim 4, wherein the hollow tube is configured to allow the at least one stabilizing mechanism to modify the geometric D shape.

6. The device of claim 5, wherein the hollow tube is configured to allow the modification after deployment of at least one of the plurality of anchor deployment zones.

7. The device of claim 1, wherein the plurality of anchor deployment zones are selected from at least one of: a first anterior anchoring zone, a second anterior anchoring zone, a posterior anchoring zone, a septal anchoring zone, and an AV node anchoring zone.

8. The device of claim 1, wherein the at least one snap mechanism is configured to be removably attached to a delivery system.

9. The device of claim 1, wherein the at least one anchor stop mechanism is configured to hold the plurality of anchors in place until deployment.

10. The device of claim 9, wherein the at least one anchor stop mechanism is associated with at least one of the plurality of anchor deployment zones.

* * * * *